US012656337B2

(12) United States Patent
Canale

(10) Patent No.: US 12,656,337 B2
(45) Date of Patent: Jun. 16, 2026

(54) COLOR-BASED BREAST MILK ANALYSES USING TEST STRIPS

(71) Applicant: Lactation Lab Inc., Santa Monica, CA (US)

(72) Inventor: Stephanie Canale, Santa Monica, CA (US)

(73) Assignee: Lactation Lab Inc., Santa Monica, CA (US)

( * ) Notice: Subject to any disclaimer, the term of this patent is extended or adjusted under 35 U.S.C. 154(b) by 1034 days.

(21) Appl. No.: 17/827,683

(22) Filed: May 28, 2022

(65) Prior Publication Data

US 2023/0384293 A1 Nov. 30, 2023

(51) Int. Cl.
| | |
|---|---|
| *G01N 33/52* | (2006.01) |
| *G01N 21/78* | (2006.01) |
| *G01N 33/66* | (2006.01) |
| *G01N 33/68* | (2006.01) |
| *G01N 33/92* | (2006.01) |
| G01N 21/77 | (2006.01) |

(52) U.S. Cl.
CPC ........... *G01N 33/521* (2013.01); *G01N 21/78* (2013.01); *G01N 33/66* (2013.01); *G01N 33/6827* (2013.01); *G01N 33/92* (2013.01); *G01N 2021/7759* (2013.01)

(58) Field of Classification Search
CPC .. G01N 33/521; G01N 33/66; G01N 33/6827; G01N 33/92; G01N 2021/7759; G01N 21/78
USPC ...... 422/420, 430, 74; 436/22, 23, 164, 165, 436/166, 169; 435/28
See application file for complete search history.

(56) References Cited

U.S. PATENT DOCUMENTS

| | | | | |
|---|---|---|---|---|
| 5,110,724 A | * | 5/1992 | Hewett | .................... C12Q 1/60 |
| | | | | 435/14 |
| 6,699,720 B1 | * | 3/2004 | Lee | ......................... G01N 33/52 |
| | | | | 436/175 |

(Continued)

FOREIGN PATENT DOCUMENTS

WO 2021/007671 A1 * 1/2021

OTHER PUBLICATIONS

Sozgen et al. Talanta, vol. 68, Sep. 19, 2005, pp. 1601-1609.*

*Primary Examiner* — Maureen Wallenhorst
(74) *Attorney, Agent, or Firm* — MEDLER FERRO WOODHOUSE & MILLS PLLC

(57) ABSTRACT

Color-based (colorimetric) breast milk analyses using test strips (paper-based assays) read with the smartphone camera to quantify the concentration in accordance with embodiments of the invention are disclosed. In one embodiment, a color-based strip for testing breast milk is provided, the strip including: a first portion including a protein reagent pad where exposing the protein reagent pad to breast milk results in a first reaction for measurement of total protein concentration in the breast milk, a second portion including a fat reagent pad where exposing the fat reagent pad to breast milk results in a second reaction for measurement of fat concentration in the breast milk, and a third portion that is or includes a lactose reagent pad where exposing the lactose reagent pad to breast milk results in a third reaction for measurement of lactose concentration in the breast milk.

8 Claims, 24 Drawing Sheets
(20 of 24 Drawing Sheet(s) Filed in Color)

Color Intensity changes on each reagent pad as concentration increases

408

402
Carbohydrates

404
Fat

406
Protein

400

(56)　　　　　References Cited

U.S. PATENT DOCUMENTS

| | | | |
|---|---|---|---|
| 2004/0219624 A1 | 11/2004 | Teodorcyzk | |
| 2007/0059678 A1* | 3/2007 | King | B01L 3/5023 |
| | | | 435/4 |
| 2007/0077168 A1* | 4/2007 | Szalczyk | G01N 33/98 |
| | | | 422/400 |
| 2008/0118615 A1 | 5/2008 | Hartmann et al. | |
| 2010/0086616 A1* | 4/2010 | Jumonville | C12Q 1/26 |
| | | | 435/28 |
| 2015/0359458 A1* | 12/2015 | Erickson | A61B 5/1495 |
| | | | 382/133 |
| 2017/0298410 A1 | 10/2017 | Jumonville | |
| 2019/0388501 A1* | 12/2019 | Deliencourt-Godefroy | |
| | | | A61K 31/70 |
| 2020/0003698 A1* | 1/2020 | Lu | G06V 20/10 |
| 2020/0393376 A1 | 12/2020 | Orbach et al. | |
| 2021/0231656 A1 | 7/2021 | Orbach et al. | |
| 2021/0247361 A1 | 8/2021 | Valster et al. | |
| 2021/0255110 A1 | 8/2021 | Beck et al. | |
| 2023/0347337 A1* | 11/2023 | Zhang | G01N 31/22 |

* cited by examiner

102

104

106

100

142

144

146

148

150

152

140

202

204

200

542

544

546

548

540

600

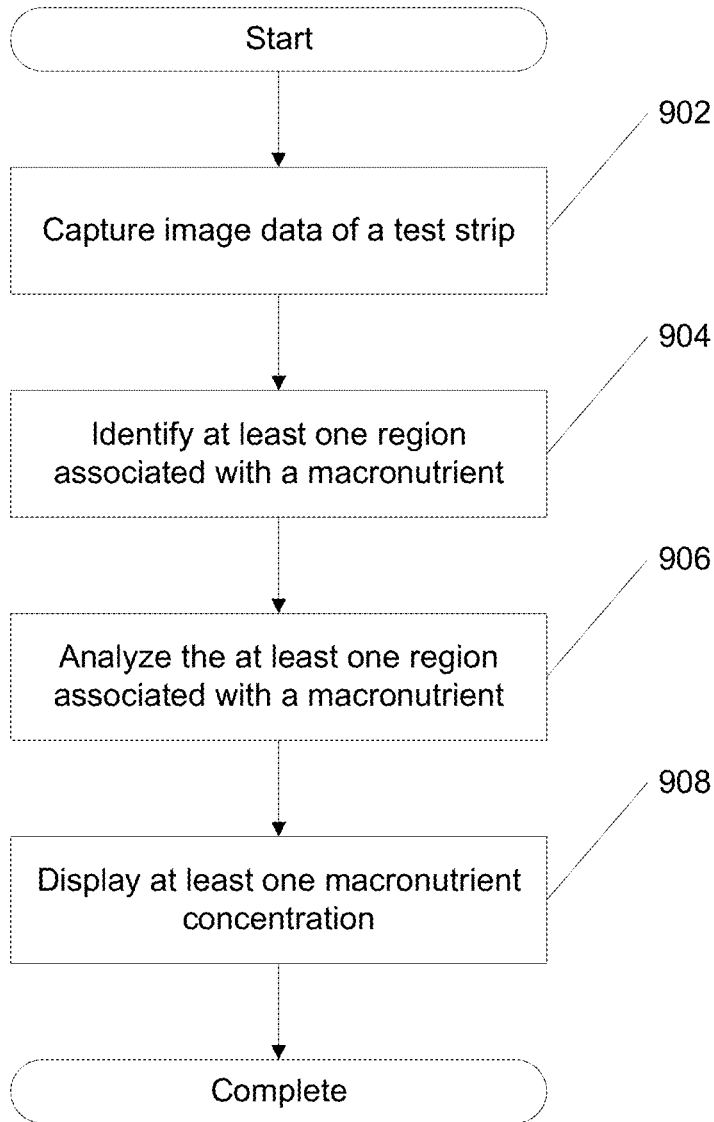
Start
902
Capture image data of a test strip
904
Identify at least one region
associated with a macronutrient
906
Analyze the at least one region
associated with a macronutrient
908
Display at least one macronutrient
concentration
Complete
FIG. 9
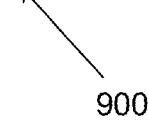
900

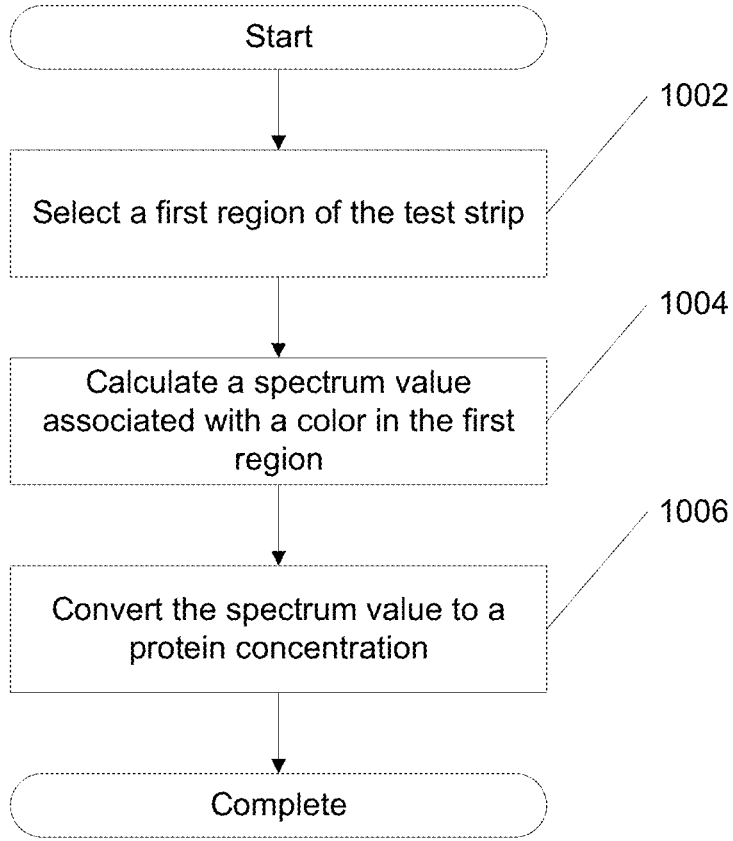
Start
1002
Select a first region of the test strip
1004
Calculate a spectrum value associated with a color in the first region
1006
Convert the spectrum value to a protein concentration
Complete
FIG. 10
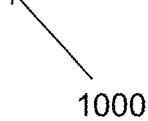
1000

Start

1102

Select a second region of the test strip

1104

Calculate a spectrum value associated with a color in the second region

1106

Convert the spectrum value to a fat concentration

Complete

1100

COLOR-BASED BREAST MILK ANALYSES USING TEST STRIPS

FIELD OF THE INVENTION

The present invention generally relates to the rapid, point of care, nutrient analyses (quantification and more specifically to color-based (colorimetric) breast milk analyses using test strips/paper-based assays read with the smartphone app).

BACKGROUND

The neonatal period marks a critical time at which undernutrition results in debilitating life-threatening illness, irreversible brain damage and impaired neurocognitive impairments. Premature infants have substantially greater nutrient requirements than full term infants. Postnatal growth restriction is a critical issue for premature infants and aggressive strategies to address target macronutrient intake are critical to assure the best possible neurodevelopmental outcomes. Nutritional support and intervention for premature infants with breast milk (BM) improves feeding tolerance, promotes intestinal mobility reducing intestinal permeability which is thought to be the mechanism behind the reduced incidence of NEC (necrotizing enterocolitis), decreases sepsis and hospital costs.

Despite the beneficial advantages associated with the early BM use, postnatal nutritional deficits and growth restriction during the neonatal period are associated with long term health and neurodevelopment outcomes. BM alone is not adequate to meet the needs of premature infants due to the macronutrient variability amongst mothers and higher nutritional needs of preterm neonates and infants. Without adequate macronutrients such as protein and energy, there is a substantial alteration in the growth trajectory of the brain and may also result in poor renal function. Although BM is best for neonates, it alone does not provide sufficient nutrition for premature infants and as such it is standard practice to fortify BM for premature infants. The quantification of macronutrients allows for precise fortification. This device is designed to be used in hospital settings, clinics by physicians, nurses, allied health care personnel (e.g., but not limited to lactation consultants and dieticians) for home use.

SUMMARY OF THE INVENTION

The various embodiments of the present colorimetric breast milk (BM) analyses using test strips or paper-based assays (may also be referred to as "BM test strips") contain several features, no single one of which is solely responsible for their desirable attributes. Without limiting the scope of the present embodiments, their more prominent features will now be discussed below. In particular, the present color-based BM analyses will be discussed in the context of BM. However, the use of BM is merely exemplary and various other substances that may be consumed for nutrients may be utilized for macronutrients (e.g., carbohydrates, fats, protein) as appropriate to the requirements of a specific application in accordance with various embodiments of the invention. Further, the present colorimetric BM analyses will be discussed in the context of test strips. However, the use of test strips is also merely exemplary and various other modes or platforms may be used for receiving and chemically interacting with substances (e.g., BM) as appropriate to the requirements of a specific application in accordance with various embodiments of the invention. After considering this discussion, and particularly after reading the section entitled "Detailed Description," one will understand how the features of the present embodiments provide the advantages described here.

One aspect of the present embodiments includes the realization that targeted (individualized) fortification may be based on testing sample milk for known concentrations of macronutrients and fortifying each feed accordingly for precise intake and may be recommended as BM without fortification typically does not meet all the nutritional requirements of preterm neonates. To provide premature infants the best possible chances at successful growth, decreased rates of NEC and improved long-term outcomes strategies may be used for targeted individualized fortification or any time a clinical need to know the nutritional composition of milk.

Another aspect of the present embodiments includes the realization that rapid quantification of macronutrient concentration in breast milk may allow for fortification (supplementation) of breast milk ensuring that premature newborns receive the nutrients they may require. This may ensure that the American Academy of Pediatrics (AAP) and European Society of Paediatric Gastroenterology, Hepatology and Nutrition (ESPGHAN) requirements are met with each feed, improving growth and decreasing morbidity and mortality amongst the most vulnerable neonates and infants.

Another aspect of the present embodiments includes the realization that current systems and devices for breast milk analyses cannot provide accurate measurements of macronutrient concentrations. For example, infrared, near-infrared and mid-infra-red milk analyzers, including MIRIS (currently the only FDA approved device), publishes a 15% error rate in fat, 12% error rate for protein and 15% error for carbohydrates. The present embodiments solve this problem by utilizing colorimetric/enzymatic breast milk analyses using client devices. The present embodiments thus advantageously and more accurately enable accurate and fast tests for nutrient concentrations in the breast milk. The present embodiments provide these advantages and enhancements, as described below.

In a first aspect, a blank strip for testing breast milk is provided, the strip including: a first portion including a protein reagent pad, where exposing the protein reagent pad to breast milk results in a first enzymatic reaction for measurement of protein concentration in the breast milk; and the protein reagent pad includes at least one protein test enzyme and the protein pad has a baseline color of green which, upon exposure to the breast milk, produces a color change to purple, where an intensity of the purple is proportional to the protein concentration in the breast milk. This allows for quantification of total protein in milk.

In an embodiment of the first aspect, the protein reagent pad tests the protein concentration using a modified BCA assay.

In another embodiment of the first aspect, the modified BCA assay uses copper (II)-neocuproine and a chromophore.

In another embodiment of the first aspect, the protein reagent pad has a test range of 0.1-5.0 g/dl.

In another embodiment of the first aspect, the protein reagent pad uses a working solution made by mixing a first reagent and a second reagent, where the second reagent is 2-4 gm cupric sulfate in 10 ml distilled water.

In another embodiment of the first aspect, the protein concentration is derived by calculating a first spectrum value (should we mention image is split into three different color channels R, B, G) associated with the intensity of purple and converting the first spectrum value to the protein concentration (quantification) based on a pre-loaded calibration curve.

In another embodiment of the first aspect, the strip further includes a second portion including a fat reagent pad, where exposing the fat reagent pad to breast milk results in a second enzymatic reaction for measurement of fat concentration in the breast milk; and the fat reagent pad includes at least one fat test enzyme and the fat pad has a baseline color of off white which, upon exposure to the breast milk, produces a color change to pink, where an intensity of the pink is proportional to the fat concentration (quantification) in the breast milk.

In another embodiment of the first aspect, the at least one fat test enzyme includes one or more Lipoprotein Lipase, G-30, Horseradish peroxidase, and Galactose kinase.

In another embodiment of the first aspect, the fat reagent pad tests the fat concentration based on a measurement of total triglycerides.

In another embodiment of the first aspect, the measurement of the triglycerides is based on an enzymatic hydrolysis of triglycerides to glycerol and free fatty acids.

In another embodiment of the first aspect, the measurement of the triglycerides further based on a measurement of released glycerol.

In another embodiment of the first aspect, the fat reagent pad has a test range of 0.5-10.0 g/dl.

In another embodiment of the first aspect, the fat concentration is derived by calculating a second spectrum value associated with the intensity of the pink and converting the second spectrum (after splitting the image into R, B, G, channels) value to the fat concentration (based on a pre-loaded calibration curve). This allows for the quantification of fat as measured by triglycerides in milk.

In another embodiment of the first aspect, the strip further includes a third portion including a lactose reagent pad, where exposing the lactose reagent pad to breast milk results in a third enzymatic reaction for measurement of lactose concentration in the breast milk; and the lactose reagent pad includes at least one lactose test enzyme and the lactose reagent pad has a baseline color of light green which, upon exposure to the breast milk, produces a color change from blue to yellow-green, where an intensity of blue or yellow is proportional to the lactose concentration in the breast milk.

In another embodiment of the first aspect, the at least one test lactose enzyme includes one or more beta-galactosidase, peroxidase and galactose oxidase.

In another embodiment of the first aspect, the at least one test lactose enzyme includes one or more beta-galactosidase, peroxidase and galactose oxidase.

In another embodiment of the first aspect, the lactose reagent pad has a test range of 5-10 g/dl.

In another embodiment of the first aspect, the lactose reagent pad uses a working solution made by mixing a buffer, an enzyme and a chromogen solution.

In another embodiment of the first aspect, the buffer includes a citrate buffer and is adjusted to pH=6.0 ranging from 5-8

In another embodiment of the first aspect, the lactose concentration is derived by calculating a third spectrum (after splitting the image into three color channels R, B, G) value associated with the intensity of the green and converting the third spectrum value to the lactose concentration and thus the quantification of lactose in milk by using a pre-loaded calibration curve.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The various embodiments of the present colorimetric BM analyses now will be discussed in detail with an emphasis on highlighting the advantageous features. These embodiments depict the novel and non-obvious colorimetric BM analyses shown in the accompanying drawings, which are for illustrative purposes only. These drawings include the following figures:

FIG. 9 is a flow chart illustrating a process for testing breast milk for macronutrient concentration(s) using a test strip in accordance with an embodiment of the invention.

FIG. 10 is a flow chart illustrating a process for analyzing a first region (reagent pad) of a test strip for protein concentration in accordance with an embodiment of the invention.

DETAILED DESCRIPTION OF THE DRAWINGS

Figure 1A:
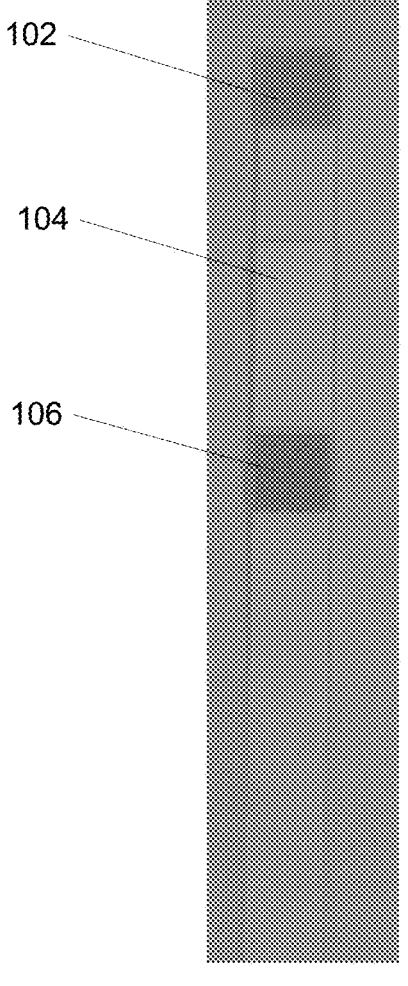
FIG. 1A is a diagram illustrating a breast milk test strip in accordance with an embodiment of the invention.

The following detailed description describes the present embodiments with reference to the drawings. In the drawings, reference numbers, label elements of the present embodiments. These reference numbers are reproduced below in connection with the discussion of the corresponding drawing features.

Turning now to the drawings, color-based breast milk analyses using test strips are provided. In many embodiments, a client device may be used to measure macronutrients in breast milk, including, but not limited to, concentrations of protein, fat, and carbohydrates (e.g., lactose). In various embodiments, color-based breast milk analyses may include using an enzyme-based test strip a plurality of reagent pads that may each change color with color intensity proportional to a concentration of a macronutrient. For example, each of the plurality of reagent pads may include a specific chemical coating that produces specific enzymatic reactions coupled with a colorimetric dye, resulting in a color change on the test strip depending on the concentration of macronutrient (e.g., fat, carbohydrates, and/or protein, and micronutrients: not limited to vitamins, minerals and other analytes) present in the breast milk sample. Each of the reagent pads uses a novel chemistry made from a novel composition of chemistry, making the reagent pad more stable, as described below. As a result of the novel chemistry, each of the reagent pads has a novel color scheme, making it more accurate for examination. Further the image processing capabilities of the app allow for quantification of each analyte.

In some embodiments, a client device having a camera may be used to capture the color change and the color intensity. For example, test strips may be scanned using a built-in camera of client devices such as, but not limited to, smart phones, tablets, etc. In several embodiments, the cameras may be used to measure absorbance of light (e.g., color intensity) for macronutrient concentration quantification. In some embodiments, the use of a camera may be more sensitive and thus more accurate as opposed to comparison of colors with the naked eye. In many embodiments, color-based breast milk analyses using test strips may also be utilized to determine total energy (e.g., calories) of a breast milk sample and/or other clinical assessments, as further described below. In addition, color-based breast milk analyses using test strips may aid in the nutritional management of newborns and infants. BM analyses using client devices in accordance with embodiments of the invention are further discussed below.

Color-Based Breast Milk Analyses Using Client Devices

Macronutrient breast milk test strips and associated client device applications (e.g., smartphone applications) may create an analytical system for measuring the concentration of fat, carbohydrates (e.g., lactose), and protein in human milk. These measurements are then used to calculate the energy (calories of the sample). As further described below, the present embodiments may be utilized at point of care using enzyme-based (colorimetric) test strips with various reagent pads. For example, a test strip may include three or more different reagent pads. Further, a smartphone camera and application may operate as a spectrometer to measure the color change on the various reagent pads which may then be used to calculate macronutrient concentrations, as further described below.

In many embodiments, these measurements may determine the total energy (calories) of a breast milk sample and in combination with other clinical assessments, may be used to aid in the nutritional management of newborns, allowing for rapid measurement of essential macronutrients in milk.

A diagram illustrating a breast milk test strip (may also be referred to as "test strip") in accordance with an embodiment of the invention is shown in FIG. 1. The breast milk test strip 100 may include a various portions designated for a particular macronutrient. For example, the breast milk test strip 100 may include a first portion having a first regent pad 102 for testing protein concentration. Further, the breast milk test strip 100 may include a second portion having a second regent pad 104 for testing fat concentration. Moreover, the breast milk test strip 100 may also include a third portion having a third regent pad 106 for testing carbohydrates such as, but not limited to, lactose concentration. The reagent pads 102, 104, 106, have unique chemistry to quantify protein, fat and carbohydrates in breast milk, as further described below.

The reagent pads 102, 104, 106 may utilize specific colors in quantifying concentrations. In many embodiments, a camera of a user's smartphone may be used to capture image data (e.g., by taking a picture of the breast milk strip) that may be used to calculate concentrations based on color intensity based on a pre-loaded calibration curve. For example, in several embodiments, the first regent pad 102 may change from a baseline color of green to purple, where the intensity of the purple color may be used to calculate the concentration of protein in the breast milk sample. In some embodiments, the second regent pad 104 may change from a baseline color of white to pink, where the intensity of the pink color may be used to calculate the concentration of fat in the breast milk sample. In some embodiments, the third regent pad 106 may change from a baseline color of light green to purple, where the intensity of the purple color may be used to calculate the concentration of lactose in the breast milk sample.

Figure 1B:
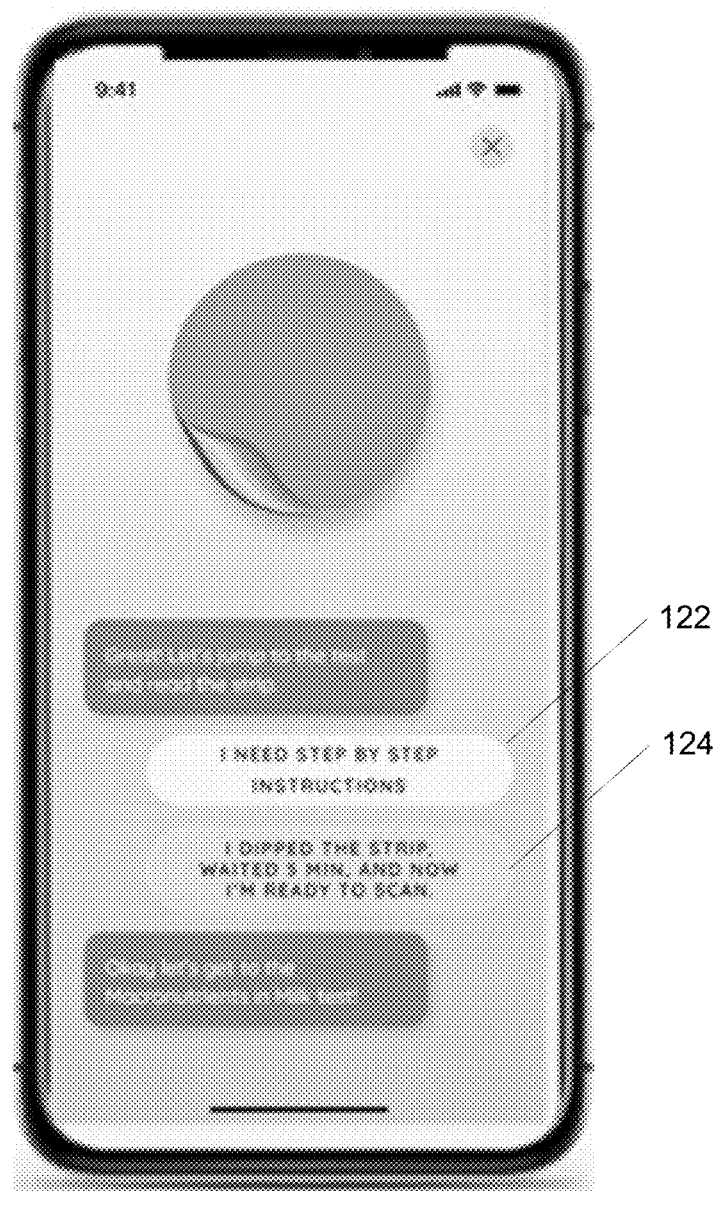
FIGS. 1B, 1C, 1D, 1E, and 1F are screen shots from the device application for testing breast milk in accordance with an embodiment of the invention.

Screen shots from a client device application for testing breast milk in accordance with an embodiment of the invention are shown in FIGS. 1B-1F. In FIG. 1B, an initial set up screen shot is illustrated. In some embodiments, the screen shot 120 may including text that helps the user begin the process of testing the breast milk. For example, the screen shot 120 may allow a user to select if they need step-by-step instructions 122 or select if they have already dipped the test strip, waited the time necessary (e.g., 5 min), and are ready to scan 124.

Figure 1C:
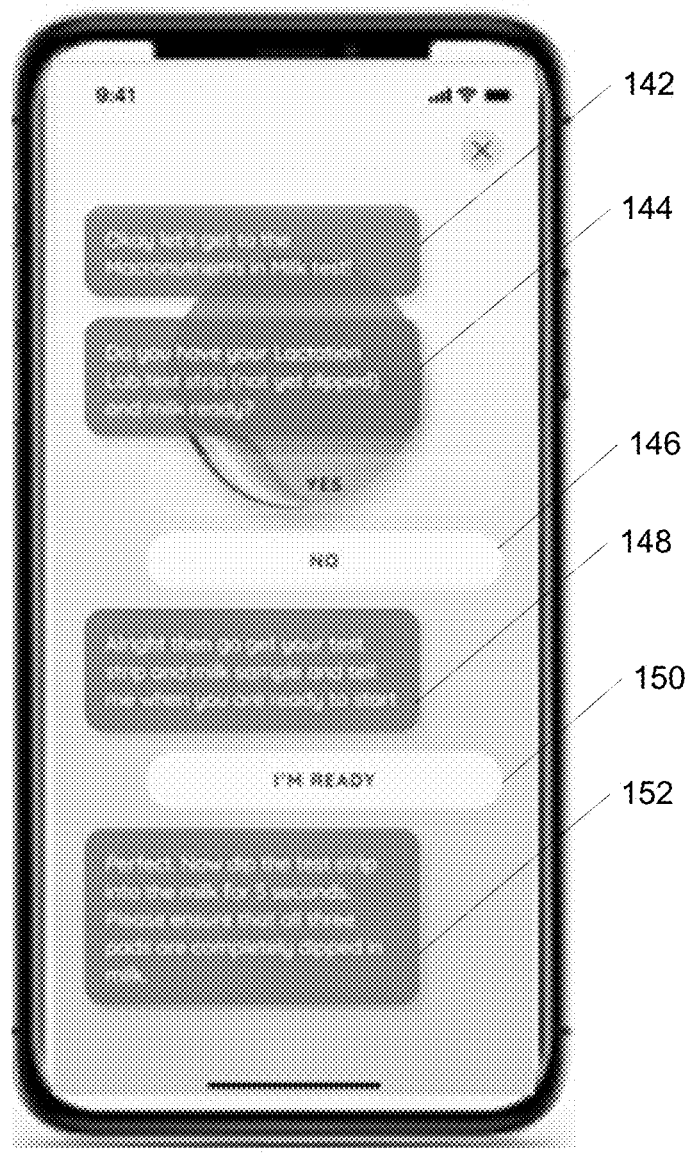

A screen shot 140 illustrating an initial step-by-step instruction is shown in FIG. 1C. In some embodiments, the screen shot 140 may instructs the user on how to begin the process of testing the breast milk. For example, the screen shot 140 may include information text 142 and a query 144 as to whether the user has the test strip and milk ready. If the user selects "no" 146, then the application may provide a prompt 148 instructing the user to get the test strip and milk sample. When the user selects that they are ready 150, then the screen shot 140 may provide further instructions 152. For example, the screen shot 140 may include a prompt 152 instructing the user to dip the test strip into the milk for a predetermine period of time such as, but not limited to 5 minutes (and can range from 2-8 minutes). The prompt 152 may also include further instructions on how to dip the test strip (e.g., to ensure that all three pads are completely dipped in the milk). In some embodiments, the instructions may be specific to a particular configuration of the test strips and testing parameters. For example, in some embodiments, the milk may be placed onto the strip as opposed to the strip being dipped into the milk. This may be particularly important in situations where the amount of milk to be tested is limited. In another example, the milk may Be dropped on the reagent pad using a dropper or pipette.

Figure 1D:
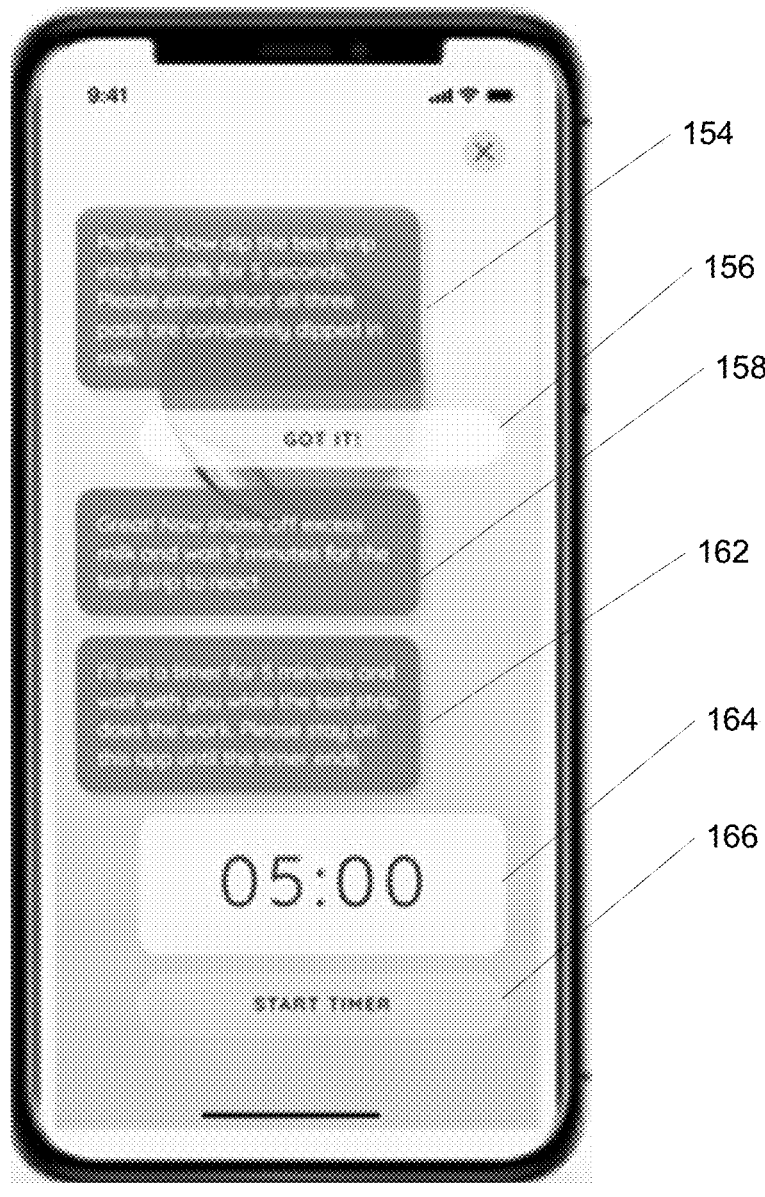

A screen shot 160 illustrating a process for dipping the test strip and beginning the timer is shown in FIG. 1D. In some embodiments, the screen shot 160 may instruct the user on how to prepare the sample on the test strip and begin the timer. For example, the screen shot 160 may include information text 154 and a user selection 156 as to whether the user has the test strip correctly dipped and ready. If the user selects "Got It!" 156, then the application may provide a prompt 158 instructing the user to shake off the excess milk and to wait the required time. A prompt 162 instructs the user that the app will provide a timer while the test strip works and further instructs the user to stay on the app until the timer ends. Timer 164 displays the countdown for the user for the allotted time remaining. When the user selects "Start Timer" 166, then the timer 164 may begin to count down. In some embodiments, the time amount may be specific to a particular configuration of the test strips and testing parameters. For example, in some embodiments, the required time to wait may be approximately three minutes. This may be particularly important in situations where a rapid test is needed.

Figure 1E:
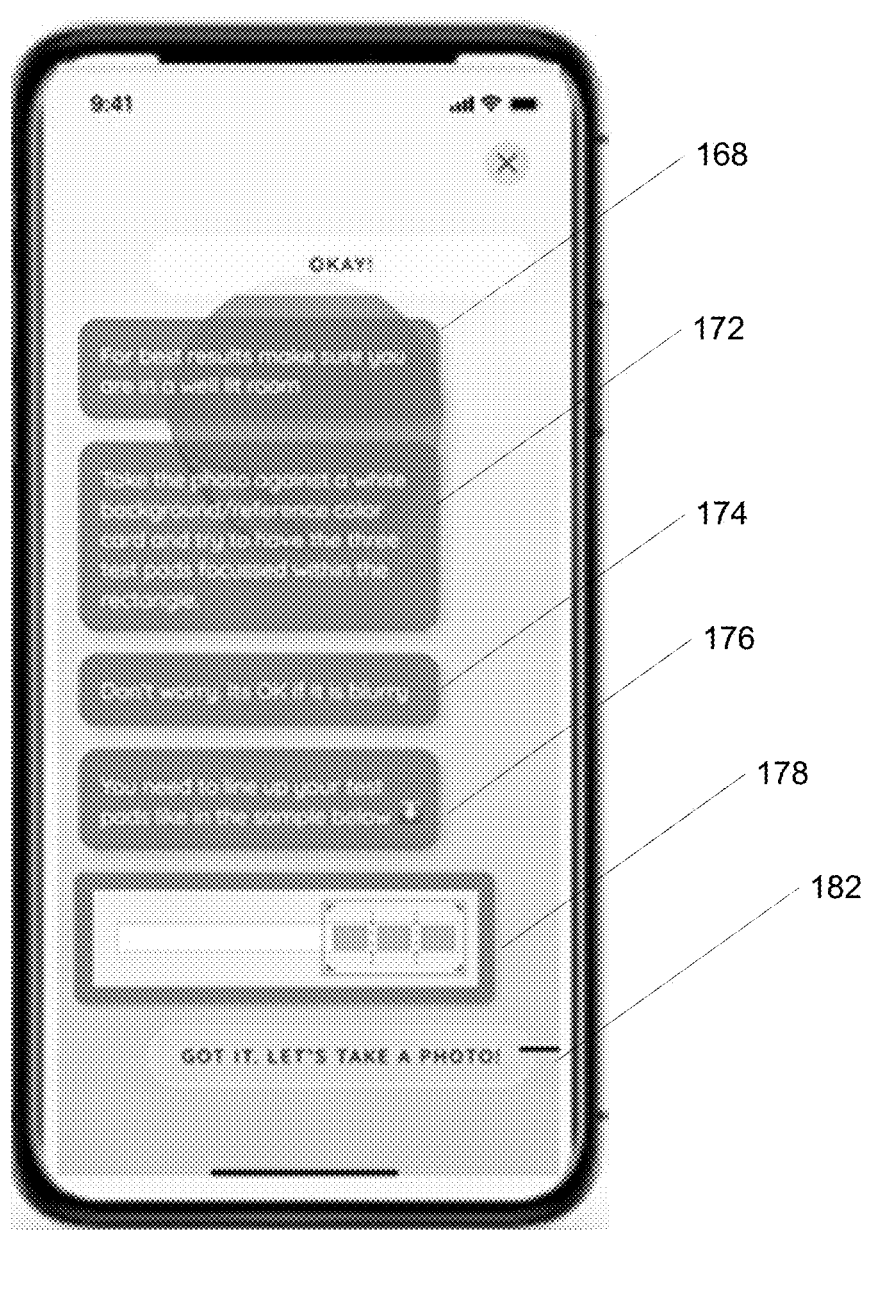

A screen shot 170 illustrating a process for taking a photo of the test strip is shown in FIG. 1E. In some embodiments, the screen shot 170 may instruct the user on how to begin the process of photographing the test strip. For example, the screen shot 170 may include information text 168 for best room lighting practices and instructions 172 for the background of the test strip photo. The screen shot 170 may include guidance 174 that it is ok if the photo is blurry. In some embodiments, the screen shot 170 will include instructions 176 that instruct a user to line up the test strip in accordance with the example 178. A user may select "Got It. let's Take a Photo!" 182 to take a photo of the test strip.

Figure 1F:
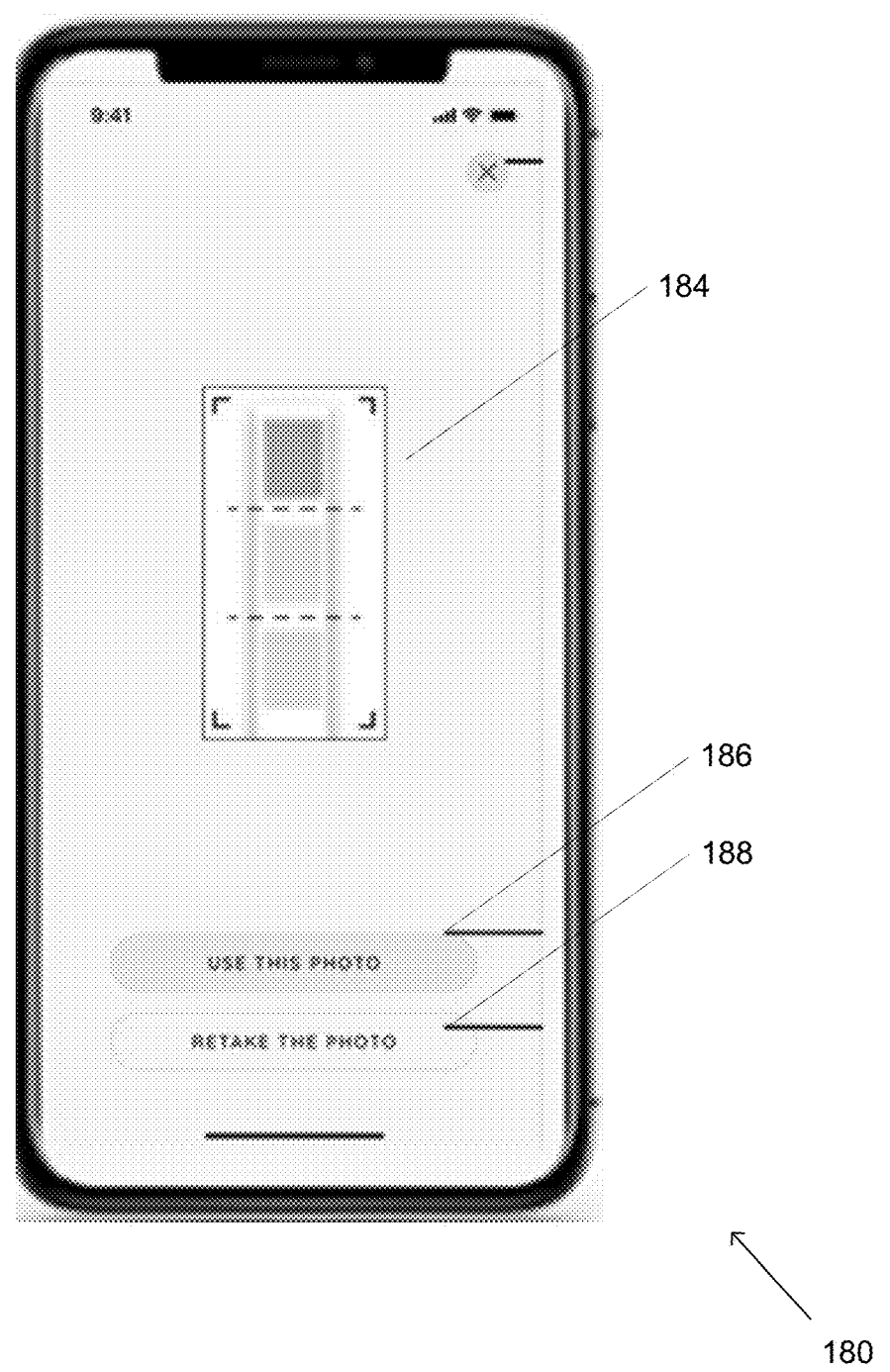

A screen shot 180 illustrating a process for selecting the photo of the test strip to use is shown in FIG. 1F. In some embodiments, the screen shot 180 may display the user photo of the test strip 184. The screen shot 180 may include options to either "Use This Photo" 186 or "Retake The Photo" 188. For example, a user may select to "Retake the Photo" 188 and go back to capture another image of the test strip.

Figure 1G:
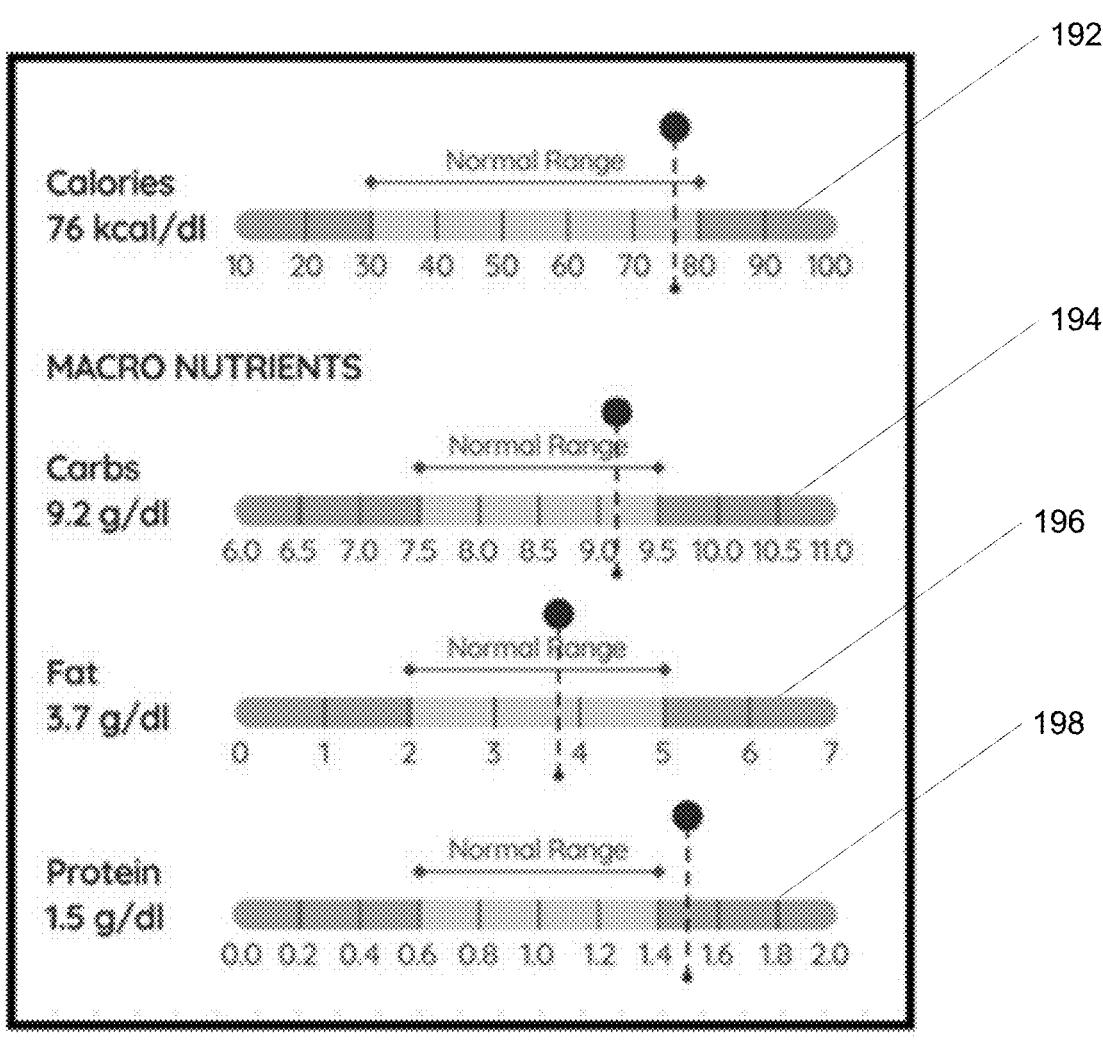
FIG. 1G illustrates a client device application displaying breast milk calories and macronutrients in accordance with an embodiment of the invention.

A screen shot 190 illustrating displayed results of the scanned test strip displayed as total fat g/dL, total protein g/dL, and carbohydrates as lactose g/dL in accordance with an embodiment of the invention is shown in FIG. 1G. In some embodiments, the result may display the normal range for each macronutrient as well as the calculated value for the breast milk sample tested. The screen shot 190 may provide Calories 192. For example, the Calories 192 may be calculated based on Protein, Fat and Carbohydrate concentrations. The screen shot 190 may also display Carbs 194, Fat 196, and Protein 198. In some embodiments, each of the displayed values may include a visual representation of the macronutrient value and show a marker of the calculated value in relation to a normal range.

Figure 2:
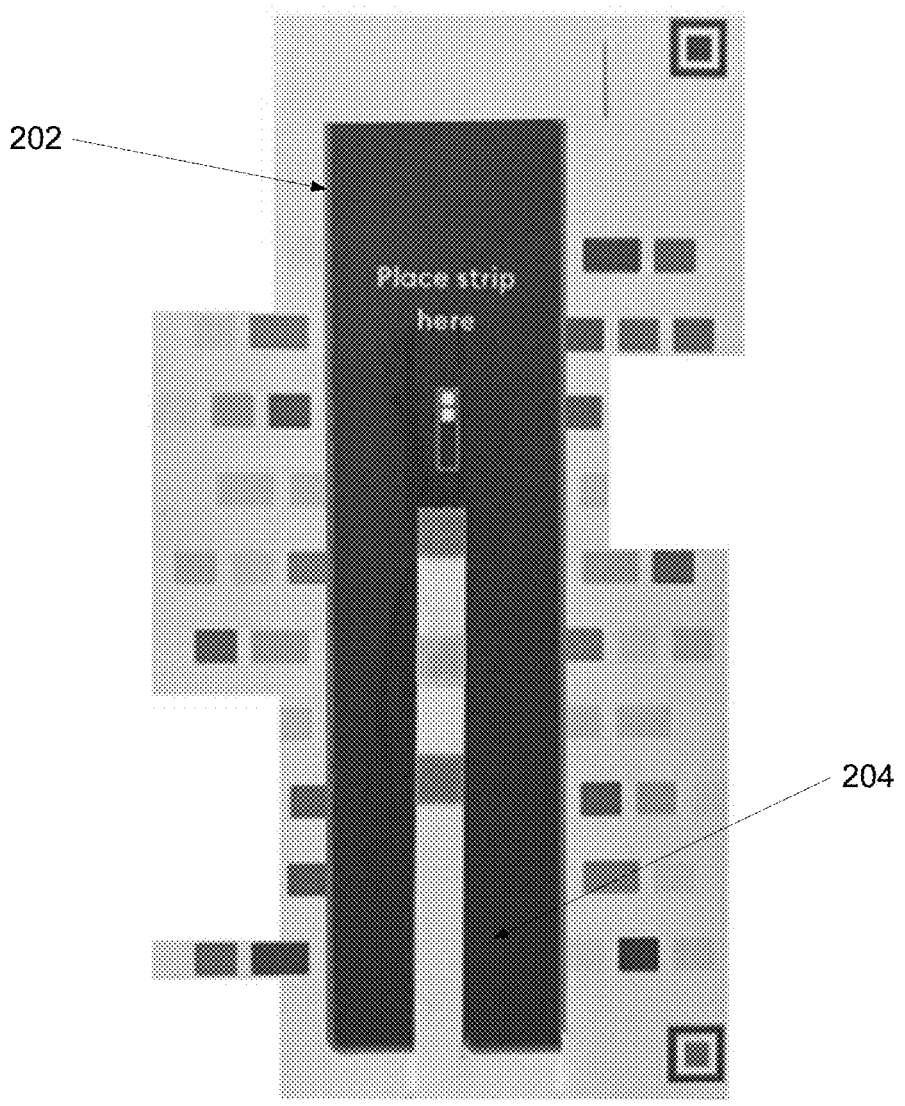
FIG. 2 illustrates an example calibration reference card for a client device in accordance with an embodiment of the invention.
Figure 2:

A calibration reference card for a client device in accordance with an embodiment of the invention is illustrated in FIG. 2. The Calibration Color Reference Card 200 may include instructions for placement of the user breast milk test strip 204 onto a test strip receiving area 202. In many embodiments, the Calibration Color Reference Card 200 may serve as a standard reference card of colors (with known chromaticity values) and allow for extraction and conversion of recorded color values of the reagent pads to values that are independent of the device and lighting. For example, the user may place the test strip dipped in breast milk on the reference color card (e.g., the test strip receiving area 202) provided after which a picture may be captured using the smartphone camera. This may be particularly important in situations where it is necessary to account for variances such as, but not limited to, lighting, angle, and other user-introduced variability. In various embodiments, the system may identify cases such as, but not limited to, when the test strip 204 is not correctly placed on the calibration color reference card 200 including the test strip receiving area 202, the calibration color reference card 200 is detected but the test strip 204 has not been placed, and/or where a blank/unused test strip has been placed on the calibration color reference card 200. In many embodiments, a user may access additional information and resources in conjunction with the breast milk test using the client device application as discussed in FIGS. 1A-1D above.

Screen shots from a client device application for testing breast milk in accordance with an embodiment of the invention are shown in FIGS. 5A-5D. In the screen shot 500 in FIG. 5A, various available resources and information available is illustrated. In some embodiments, the screen shot 500 may include a bar 502 that may allow a user to select "My baby," "explore", or "menu." For example, the screen shot 500 may allow a user to select to view the "Mom's Health & Tests" 504, a "daily journal" 506 or select to connect with a "virtual consultant" 508. In some embodiments, the screen shot 500 may also allow a user to view the "Baby's health" 510, available "resources" 512, or their "journey" 514.

Figure 5A:
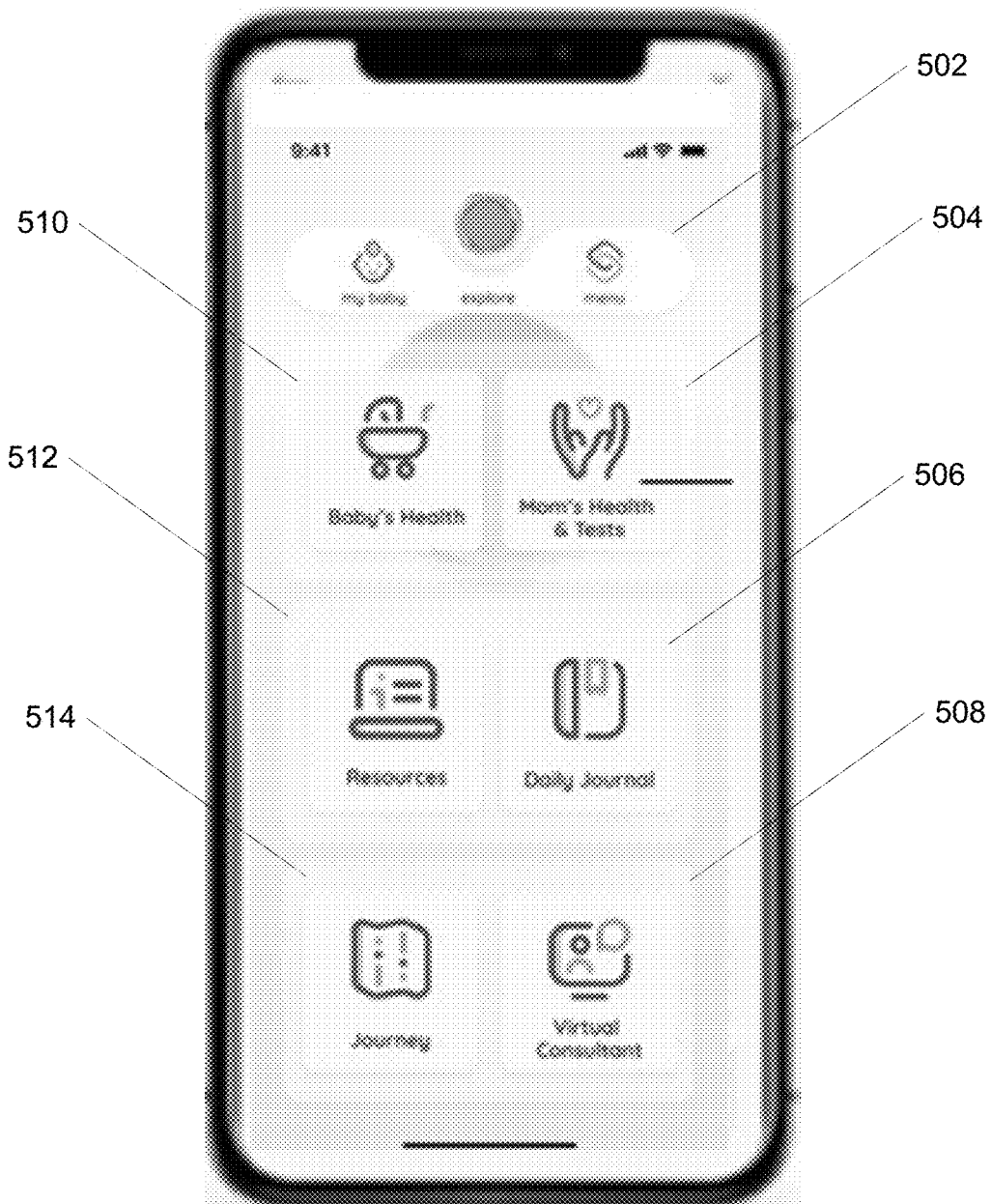
FIGS. 5A, 5B, and 5C are screen shots from a client device application for testing breast milk in accordance with an embodiment of the invention.
Figure 5B:
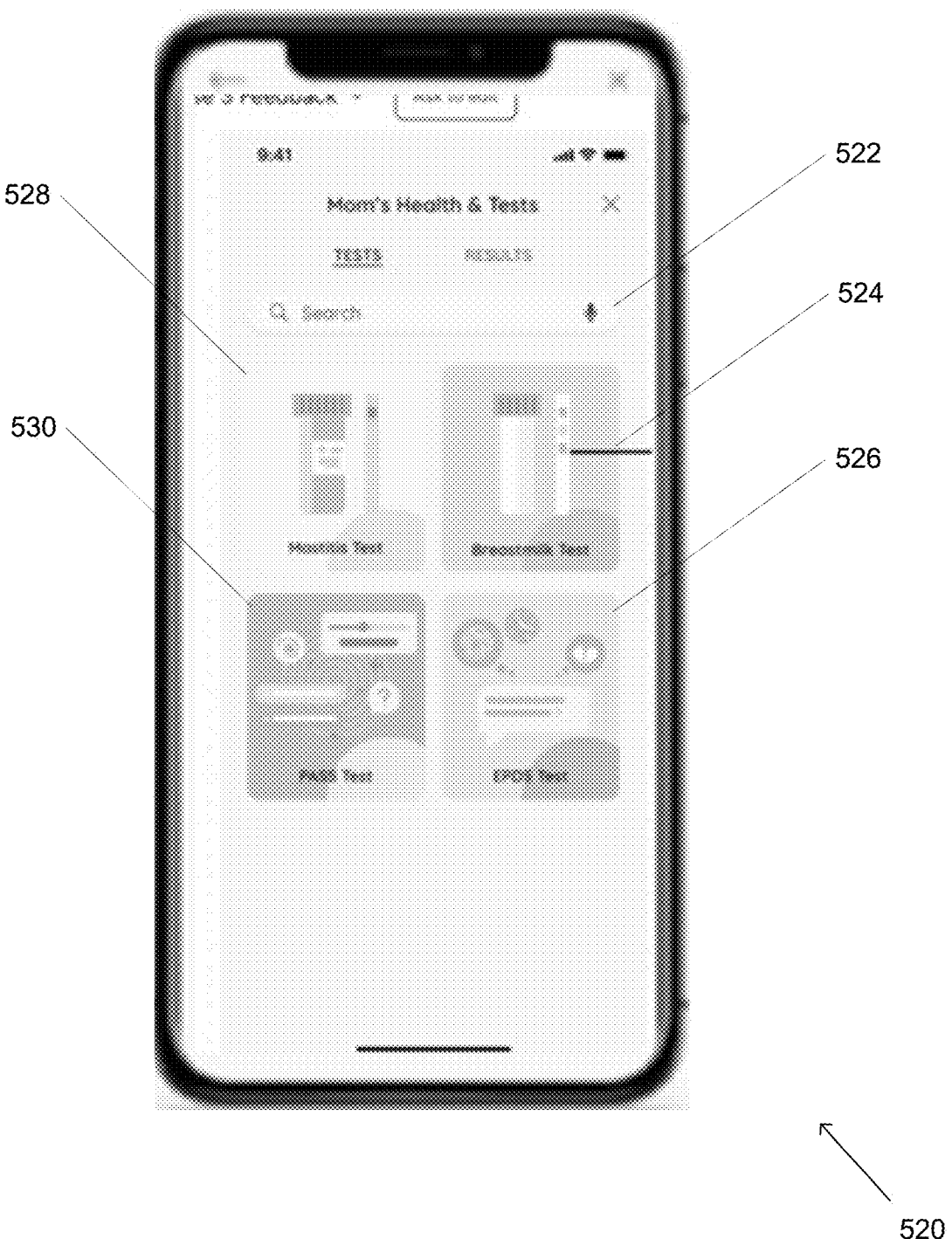

In the screen shot 520 in FIG. 5B, an embodiment of the "Mom's health & test" 520 tab is illustrated. In some embodiments, the screen shot 520 may be an embodiment of the "Mom's Health & Tests" 504 in FIG. 5A. Screen shot 520 may include a search bar 522. In various embodiments, the screen shot 520 may allow a user to select to view the "Breastmilk Test" 524, a "EPDS Test" 526. In some embodiments, the screen shot 520 may also allow a user to view the "Mastitis Test" 528 or "PASS Test" 530.

Figure 5C:
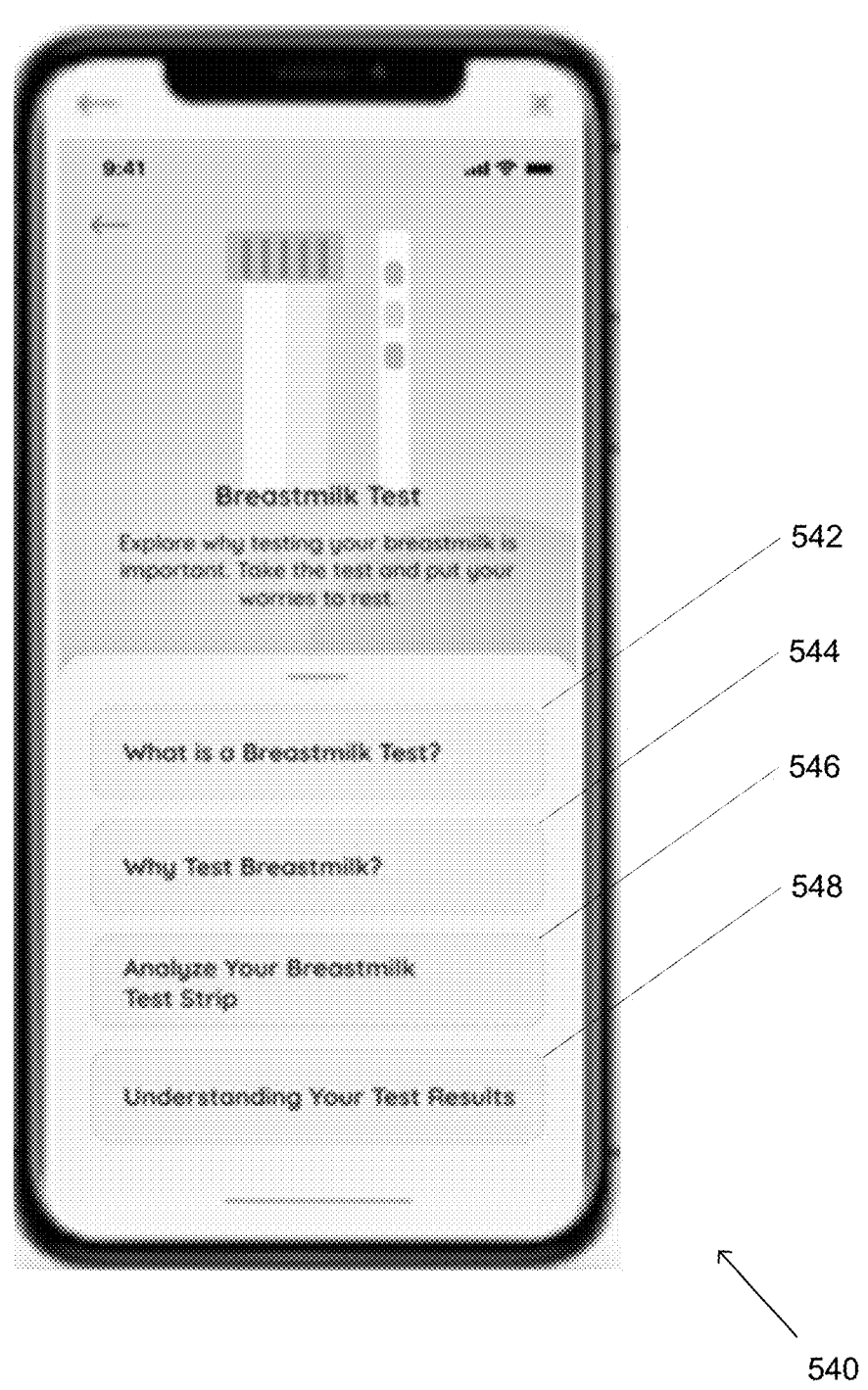

In the screen shot 540 in FIG. 5C, an embodiment of the "Breastmilk Test" tab is illustrated. In some embodiments, the screen shot 540 may be an embodiment of the "Breastmilk Test" 524 in FIG. 5B. Screen shot 540 may include a selection to understand "What is a Breastmilk Test?" 542. In various embodiments, the screen shot 540 may allow a user to select to view the "Why Test Breastmilk?" 544. In some embodiments, the screen shot 540 may enable a user to select to "Analyze Your Breastmilk Test Strip" 546 or choose help for "Understanding Your Test Results." 548. A step-by-step process of color transformation application and reagent pad extraction in accordance with embodiments of the invention are further discussed below.

Although specific test strips and client device applications for testing breast milk are discussed above with respect to FIGS. 1A-D, 2, and 5A-D any of a variety of test strips and client device applications as appropriate to the requirements of a specific application can be utilized in accordance with embodiments of the invention. Breast milk test workflows in accordance with embodiments of the invention is discussed further below.

Breast Milk Test Workflows

Figure 3:
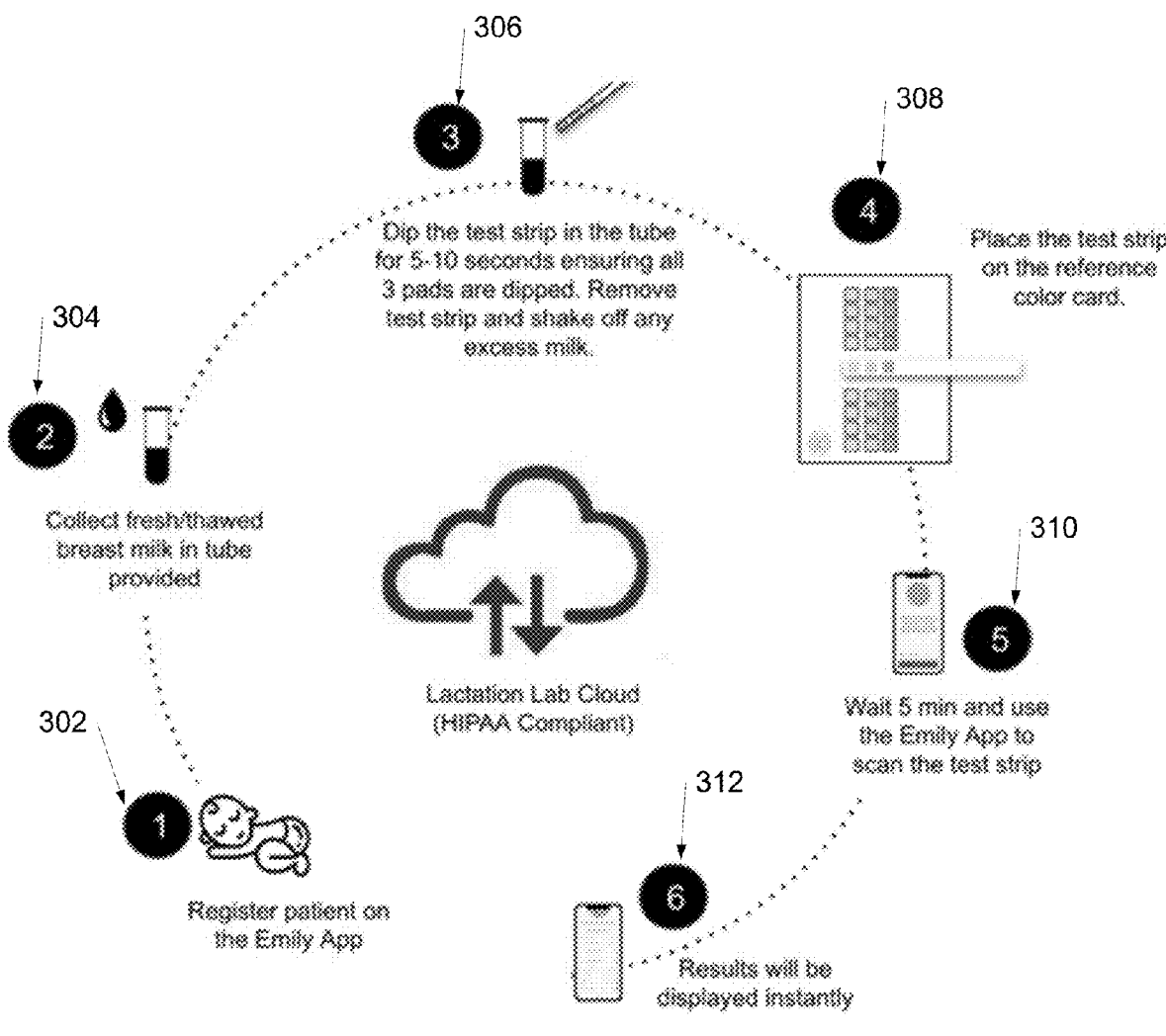
FIG. 3 illustrates a diagram of a breast milk test and client device application workflow in accordance with an embodiment of the invention.

Various workflows may be used to perform breast milk testing using breast milk test strips and the client device applications as described herein. A diagram of a breast milk test and client device application workflow in accordance with an embodiment of the invention is shown in FIG. 3. The workflow 300 may include a first step (i.e., step 1) 302, where the user may register on the client device application. The workflow 300 may also include a second step (i.e., step 2) 304, where the user may prepare breast milk to be tested. In many embodiments, the user may collect breast milk in a container. In some embodiments, the breast milk may be fresh. In some embodiments, the breast milk may be thawed or refrigerated. In many embodiments, the container may be any vessel such as, but not limited to, a tube, test tube, or bottle. Further, the workflow 300 may include a third step (i.e., step 3) 306, where the user may dip a test strip into the breast milk which is prepared in step 2 304. The User may then remove the test strip from the breast milk and shake off any excess milk. In many embodiments, the user may dip the test strip in the container for a period of time which is sufficient for each reagent on each pad to react with the breast milk. For example, in some embodiments, the user may dip the test trip in the breast milk for 5-10 seconds and ensure all reagent pads are dipped with the breast milk. In many embodiments, the test strip may show a color change on each reagent pad after the reaction. In many embodiments, the intensity of the color on each reagent pad may be based on the concentration of the macronutrient tested on the pad, as further described below.

In reference to FIG. 3, the workflow 300 may also include a fourth step (i.e., step 4) 308, where the user may place the test strip on the color calibration reference card. The color calibration reference card may be used to calibrate variations introduced by factors such as, but not limited to, observational variations of individual users, lighting conditions, etc. Furthermore, the workflow 300 may include a fifth step (i.e., step 5) 310, where the user may use the client device application to scan the test trip after the reactions on the reagent pads are finished. The captured image of the test strip may be processed by the client device application to measure the absorbance of the test strip to quantify macronutrient concentrations, as further described below. In many embodiments, the user may enable his/her client device's camera to scan the test trip. In many embodiments, the user may be provided instructions on the client device application, as described above. In addition, the workflow 300 may include a sixth step (i.e., step 6) 312, where the user may observe the test results on the client device application. The client device application may provide more precise information about the breast milk and various other information that may be useful to the user.

Although a specific breast milk test workflow is discussed above with respect to FIG. 3, any of a variety of workflows having various steps as appropriate to the requirements of a specific application can be utilized in accordance with embodiments of the invention. Reagent pads of the breast milk test strips in accordance with embodiments of the invention are discussed further below.

Reagent Pads of Test Strips

Figure 4:
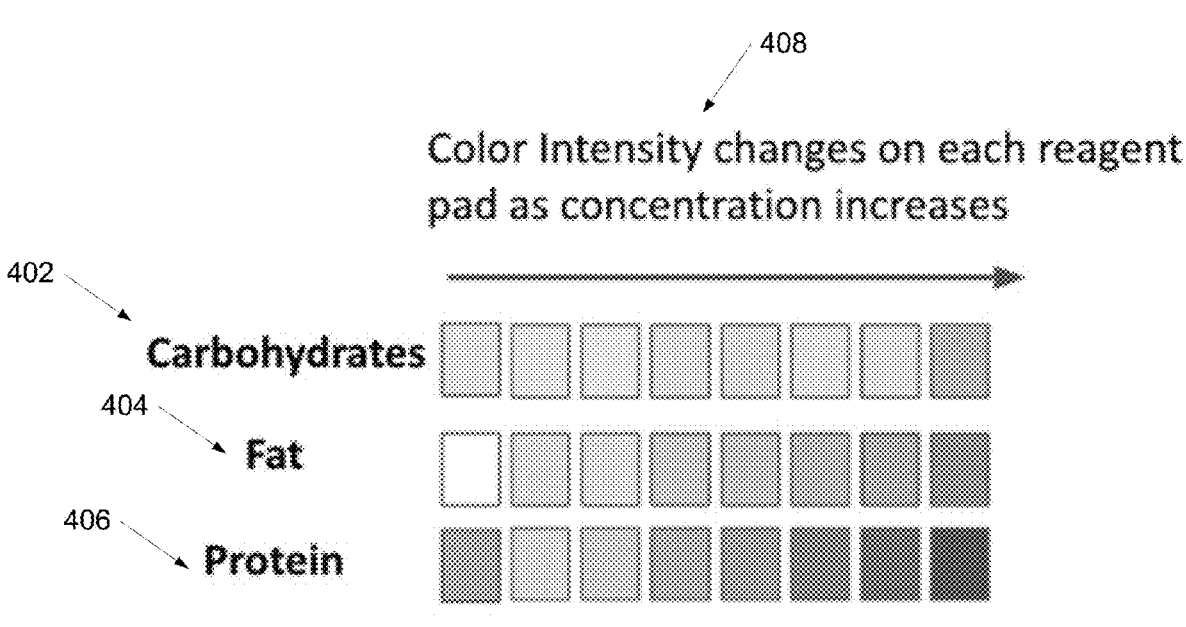
FIG. 4 illustrates color change on a reagent pad based on the concentration of a macronutrient in breast milk in accordance with an embodiment of the invention.

The reagent pads of test strips may use various assays to determine the concentrations of macronutrients. For the assays, the reagent pads may employ various compositions of chemistry, which may result in various color change schemes when exposed to breast milk. An example of color change on a reagent pad based on the concentration of a macronutrient in the breast milk in accordance with an embodiment of the invention is illustrated in FIG. 4. An example color change on the reagent pad based on concentration of macronutrient in breast milk is shown in illustration 400. Illustration 400 may include a direction 408 indicating the color intensity changes on each reagent pad as the concentration increases. In some embodiments, the leftmost color indicates the default color of the dry (unused) reagent pad. For example, the illustration 400 may include exemplary color changes for lactose reagent pad 402. The illustration 400 may also include color change examples for Fat 404 reagent pad and Protein 406 reagent pad. In several embodiments, the Carbohydrates reagent pad 402 may start as a light yellow-green color to start and change to a blue then to a yellow tone correlating with the concentration of lactose via lactose standards. In a variety of embodiments, the Fat reagent pad 404 may start as an off-white color and change to darker pink correlating with the concentration of fat. In a variety of embodiments, the Protein reagent pad 406 may start as a green color and change to a purple color wherein the intensity of the purple correlates with the concentration of protein.

The protein reagent pad may use various assays to determine the concentration of protein in the breast milk. In many embodiments, the enzymatic reaction for the protein test-pad is based on a modified BCA assay. The method specifically uses copper (II)-neocuproine and a chromophore, which is a simple, rapid, reproducible, and sensitive analysis. When the test pad gets in contact with a BSA standard solution or breastmilk sample after a period of incubation (ranging from 1-5 minutes) the assay reaction then produces a characteristic color. Protein detection ranges from 0.1-5.0 g/dl.

The protein reagent pad may employ various compositions of chemistry to react with protein. As an example, the specific composition of chemistry for the protein reagent pad is as follows. Step 1 is to make a reagent A from: a) 1.5 gm sodium bicinchoninate (BCA), b) 2 gm sodium carbonate, 0.16 gm sodium tartrate, c) 0.4 gm NaOH, and d) 0.95 gm sodium bicarbonate, brought to 100 ml with distilled water. Step 2 is to adjust the pH to 11.25 with 10 M NaOH. In some embodiments, the pH can range from 9-11.5. The solution is typically pale pink in color, clear and odorless. Step 3 is to leave the solution at room temperature. Step 4 is to make a reagent B from: 3 gm cupric sulfate (5× hydrated) in 10 ml distilled water. In some embodiments, the amount of cupric sulfate can range from 2-4 gm. The solution is typically a bright blue color. The extra copper sulfate forms a precipitate at the bottom. Step 5 is to refrigerate the solution. Step 6 is to make a standard working solution by mixing 100 volumes reagent A with 2 volumes reagent B. The stock solutions are stable. The working solution is stable for 1 week and should be green. The working solution is bright green, and the coated paper is a green color. The intensity of the purple color correlated with the amount of protein in the sample. Although the steps are shown in a specific order, the invention is not limited thereto.

The fat reagent pad may use various assays to determine the concentration of fat in the breast milk. In many embodiments, fat is measured using triglycerides. The fat in breast milk is made up of 98-99%% of triacylglycerols, therefore the colorimetric measure is of triglycerides as they are hydrolyzed completely to free fatty acids and glycerol by lipoprotein lipase, subsequently glycerol kinase, glycerol phosphate oxidase, horseradish peroxidase using a pink dye indicator the amount of total fat as measure by total glycerol correlated with the intensity of the pink dye color. The test pad develops a pink color visible with the naked eye. The intensity of the color is directly proportional to the concentration of the triglycerides present in the sample. Fat as Measured by triglycerides (98%) of total fats ranges from 0.1-10.0.0 g/dl.

The fat reagent pad may employ various compositions of chemistry to react with fat. As an example, the specific composition of chemistry for the fat reagent pad is as follows. Step 1 is to buffer. In some embodiments, the buffer can be pipes buffer and tris buffer and in other cases a phosphate buffer may be used. Step 2 is to make a 50 mM buffer 1 ml of 1 M buffer mixed with 20 ml of deionized water. The solution is typically milky color. Step 3 is to use drops of 10M NaOH solution to bring pH to 6 (can range from 4-7 (roughly one drop of 10M NAOH=0.1 change in pH). Step 4 is to make working solution from: a) 1 ml of Triton-X solution, b) 10 ml of 50 mM buffer c) one of possible indicators in the anisidine family such as but not limited to ESPA N-ethyl-N-(3-sulfulpropyl)-m-anisidine sodium salt d) CHAPS solution d) magnesium acetate 40-60 mg, e) 4-AAP 4-7 mg, and f) ATP 3 30-40 mg. In some embodiments, the pH value of the buffer can range from 4-7. In some embodiments, the concentration of CHAPS solution can range from 0.5-2%. In some embodiments, the amount of magnesium acetate can range from 30-100 mg. In some embodiments, the amount of 4-AAP can range from 3-10 mg. In some embodiments, the amount of ATP can range from 20-100 mg. Step 5 is to use a PVOH solution to dry the paper. In some embodiments, the concentration of the PVOH solution can range from 1-15%. Step 6 is to make working solution from: a) 5 ml of standard solution, In some embodiments, the amount of lipoprotein lipase can range 60-200 U. In some embodiments, the amount of G-30 can range from 60-100 U. In some embodiments, the amount of HP can range from 100-250 U. In some embodiments, the amount of GK can range from 125-300 U. In some embodiments, the CHAPS solution, triton solution and PVOH solutions including the buffer are made first. Although the steps are shown in a specific order, the invention is not limited thereto.

The lactose reagent pad may use various assays to determine the concentration of lactose in the breast milk. In many embodiments, the lactose is measured through the reaction of lactose with beta galactosidase, peroxidase and galactose oxidase enzymes. The measurement of lactose with an enzymatic color change method has been shown to be the most sensitive and specific. The enzymatic measurement of lactose in breast milk is to hydrolyze the lactose into glucose and galactose using β-galactosidase. The reaction is as follows: Lactose+$H_2O\rightarrow$Glucose+Galactose. In some embodiments, galactose oxidase and horseradish peroxidase are added to β-galactosidase and immobilized onto a paper support with an added chromogen. The strip is dipped in breast milk and forms the color that develops from the added chromogen. Lactose detection ranges from 5-10 g/dl.

As an example, the specific composition of chemistry for the lactose reagent pad is as follows. Step 1 is to make a buffer. In some embodiments, the buffer can be a citrate buffer, TRIS buffer or phosphate buffer. Step 2 is to adjust the pH of the buffer to 5-7Step 3 is to make a chromogen solution from for example using dianisidine per in buffer. Step 4 is to prepare 2 mg of ABTS per milliliter of the buffer. Step 5 is to prepare 1 mg of methyl red or bromocresol purple, per milliliter of the buffer. In some embodiments, methyl red can also be used in step 5. In some embodiments, the solution in step 5 is precipitated and then centrifuged to extract the top layer without precipitate. Step 6 is to make enzyme solution from: 40 U lactase (beta-galactosidase), 200 U horseradish peroxidase, 40 U of galactose oxidase in 100 ul of buffer, 1000 U beta-galactosidase in 25 ml of buffer, 5000 U horseradish peroxidase in 25 ml of buffer, and 1000 U of galactose oxidase in 25 ml of buffer. In some embodiments, the amount of the lactase can range from 30-60 U. In some embodiments, the amount of the horseradish peroxidase can range from 100-300 U. In some embodiments, the amount of galactose oxidase can range from 20-80 U in 100 ul of buffer. Step 7 is to mix 100 ul of enzymes and 100 ul of chromogen to 50 ul of glutaraldehyde solution. Step 8 is to prepare glutaraldehyde solution for stabilizing the solution. Stock solution in vial is 25% in 10 ml diluted with deionized water and kept at room temperature. Although the steps are shown in a specific order, the invention is not limited thereto.

Although the color change on a reagent pad based on the concentration of a macronutrient in the breast milk is discussed above with respect to FIG. 4, any of a variety of test strips and client device applications as appropriate to the requirements of a specific application can be utilized in accordance with embodiments of the invention. Similarly, although specific essays and compositions of the reagent pads are discussed above, any of a variety of essays and compositions appropriate to the requirements of a specific application can be utilized in accordance with embodiments of the invention. Color transformation application and reagent pad extraction in accordance with embodiments of the invention are further discussed below.

Color Transformation Application and Reagent Pad Extraction

Figure 6:
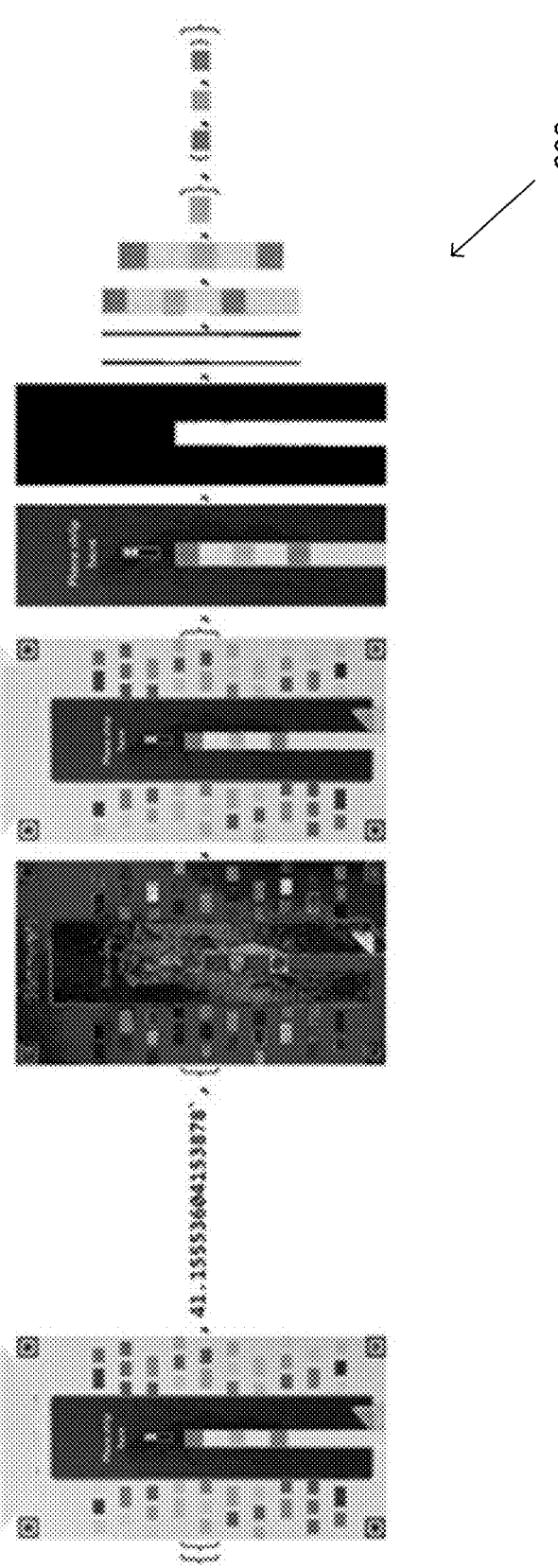
FIG. 6 illustrates a calibration reference process for the client device in accordance with an embodiment of the invention.

In some embodiments, a client application may perform a transformation of the color on the test strip using a calibration reference card as further described above. A process of color transformation application and reagent pad extraction is illustrated in FIG. 6. In some embodiments, the color correction and extraction are performed through determining the color transformation matrix and extracting the three reagent pads and their color. In various embodiments, the application may be implemented using open-source software. For example, a Histogram Transform method may be used for color correction purposes. In many embodiments, the Histogram Transform method is a point operation that changes the shape of the image histogram and may be used for equalization or matching with a reference distribution. In some embodiments, the Histogram Transform method may be applied through an interpolating function between the quantiles of image, activated test strip with the color calibration card, and reference, blank test strip with the color calibration card, and apply it to each pixel in image. In various embodiments, to correct for orientation variability of the test strip the KAZE, a nonlinear scale-space detector and/or descriptor or BRISK (Binary Robust Invariant Scalable Keypoints) may be applied. In some examples, where both these methods fail, the user may be requested to redo the test. In various embodiments, when the transformation matrix has been applied, the next step involves extracting the colors from the strip by cropping the image down to the three individual reagent pads. In some embodiments, this may be enabled by generating a ratio equation using the dimensions of the test strip. For example, for the lactose and protein reagent pads (top and bottom pads), the image is scaled down to 5 px by 30 px to average the colors and the center pixel value is selected. In many embodiments, for Glycerol which is the middle reagent pad, the edges are cropped out as well to ensure no horizontal reflected light biases the color extraction. In many embodiments, the darkest pixel value may be then chosen.

Although a specific process of color transformation application and reagent pad extraction is described above with respect to FIG. 6, any of a variety of processes for color transformations and reagent pad extractions as appropriate to the requirements of a specific application can be utilized in accordance with embodiments of the invention. Color calibration in accordance with embodiments of the invention are further discussed below.

Color Calibration

Based on the color intensity, the concentration value may be determined from the pre-calculated calibration curves created by test-retest methods. Calibration curves for pro-

US 12,656,337 B2

Figure 7A:
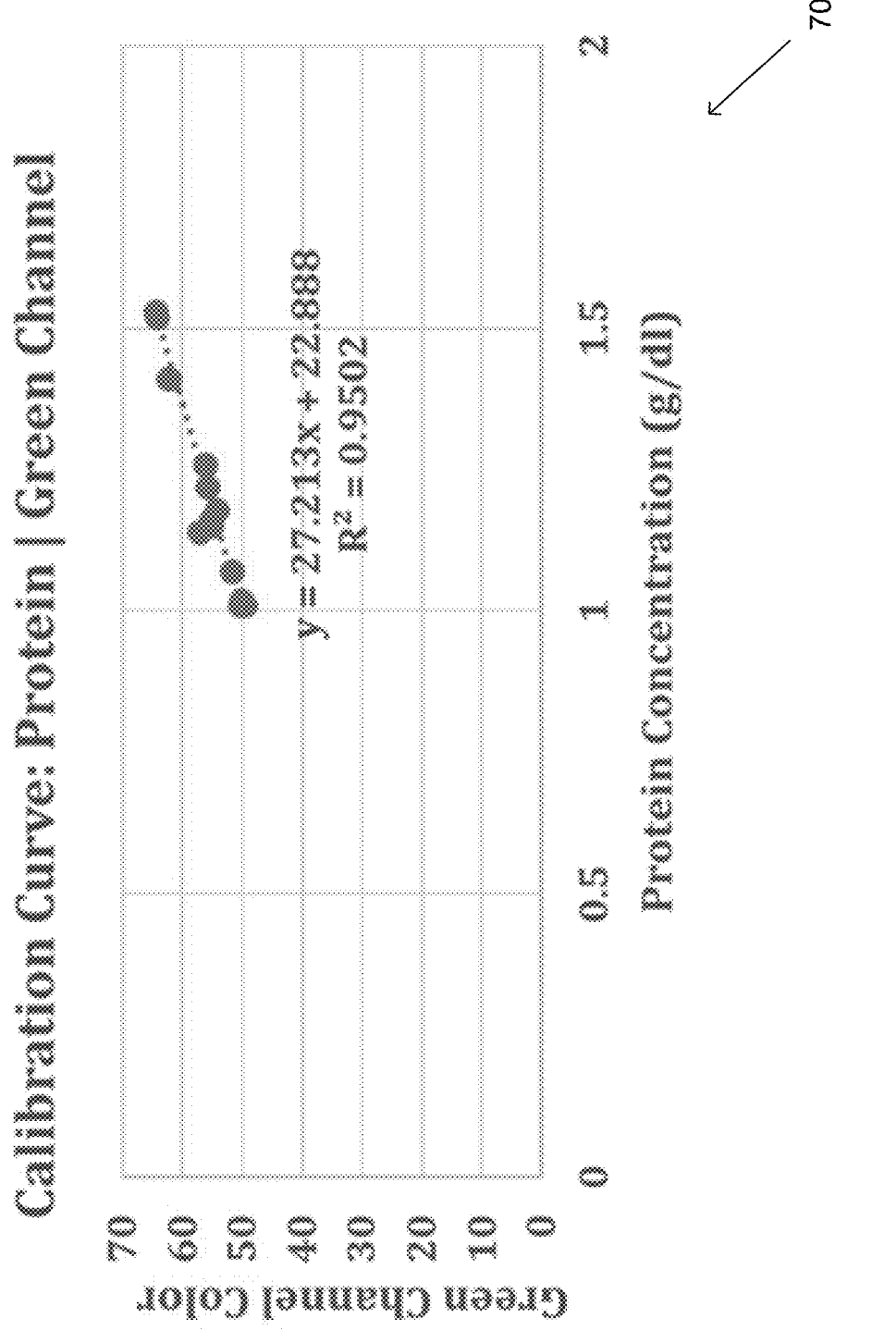
FIG. 7A illustrates a calibration curve for protein in accordance with an embodiment of the invention.
Figure 7B:
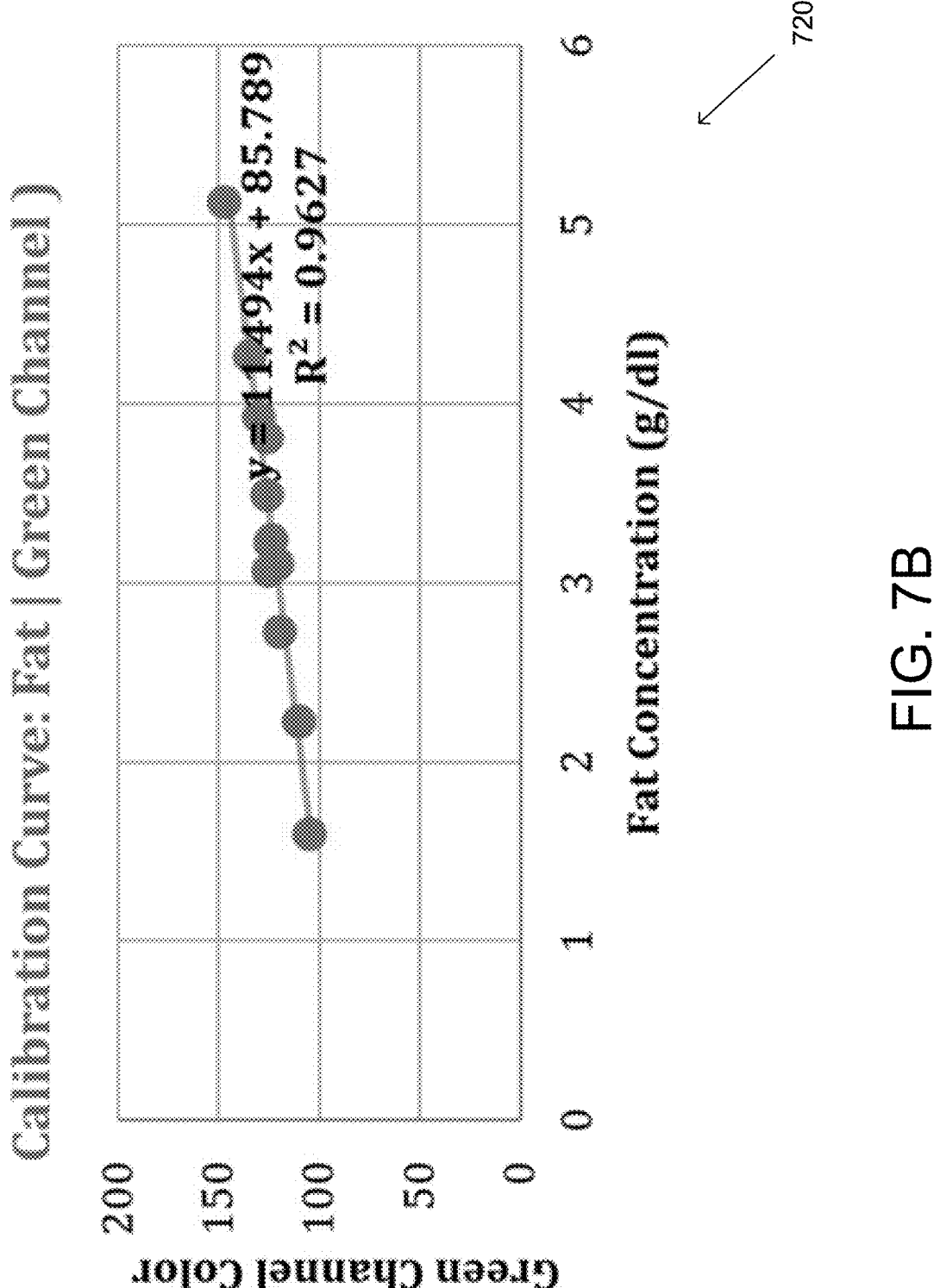
FIG. 7B illustrates a calibration curve for fat in accordance with an embodiment of the invention.
Figure 7C:
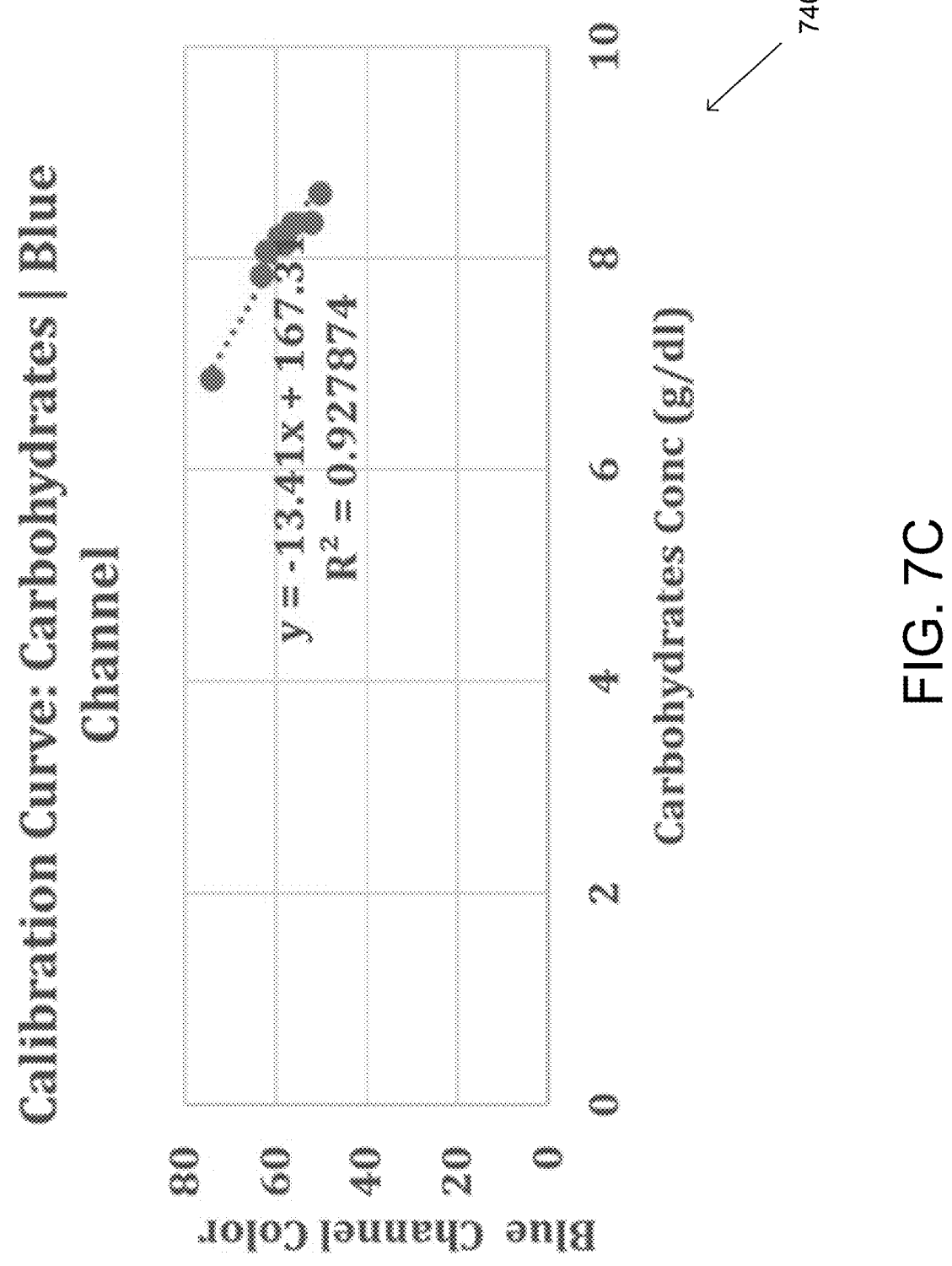
FIG. 7C illustrates a calibration curve for carbohydrates in accordance with an embodiment of the invention.

13 tein, fat and carbohydrates in accordance with an embodiment of the invention are shown FIGS. 7A, 7B and 7C, respectively. Calibration curves may be generated for each macronutrient using breast milk samples that are quantified and validated. Data for generating the calibration curves may be collected by dipping test strips in breast milk samples and imaging the test strips using a professional camera in a white photo box and in controlled settings across all data points. Each image may be split into three color channels (e.g., red, blue and green). The channel with the greatest amount of contrast may be used to analyze each reagent pad.

In some embodiments, the blue channel is chosen for lactose and the green channel is chosen for protein and fat. In some embodiments, each sample is analyzed and photographed in triplicate with a blank test strip. The intensity of the color under the reagent pad is analyzed and the average of the three readings is measured and recorded.

A concentration curve and standard equation to correlate the reagent pad color intensity against concentration is created. In some embodiments, correlation coefficients of $r^2 > 0.9$ are observed in the case of all three macronutrients that demonstrate accuracy of the test strip and the linearity of the model. These three calibration equations are then used to determine the concentration of the sample tested by inputting the corresponding color value extracted from the reagent pad.

Although a color calibration method is discussed above with respect to FIGS. 7A-7C, any of a variety of color calibration methods as appropriate to the requirements of a specific application can be utilized in accordance with embodiments of the invention. Accuracy testing and validation in accordance with embodiments of the invention is discussed further below.

Accuracy Testing and Validation

The Breast Milk Analyses are tested using samples whose macronutrient compositions are determined in a third-party lab using gold standard methods. For each of the samples, test-retest experiments are done where test strips were dipped in the same milk sample and are scanned in different lighting conditions. Post color correction, the color values are extracted for each of the test strips under each lighting condition and for each macronutrient.

Figure 8A:
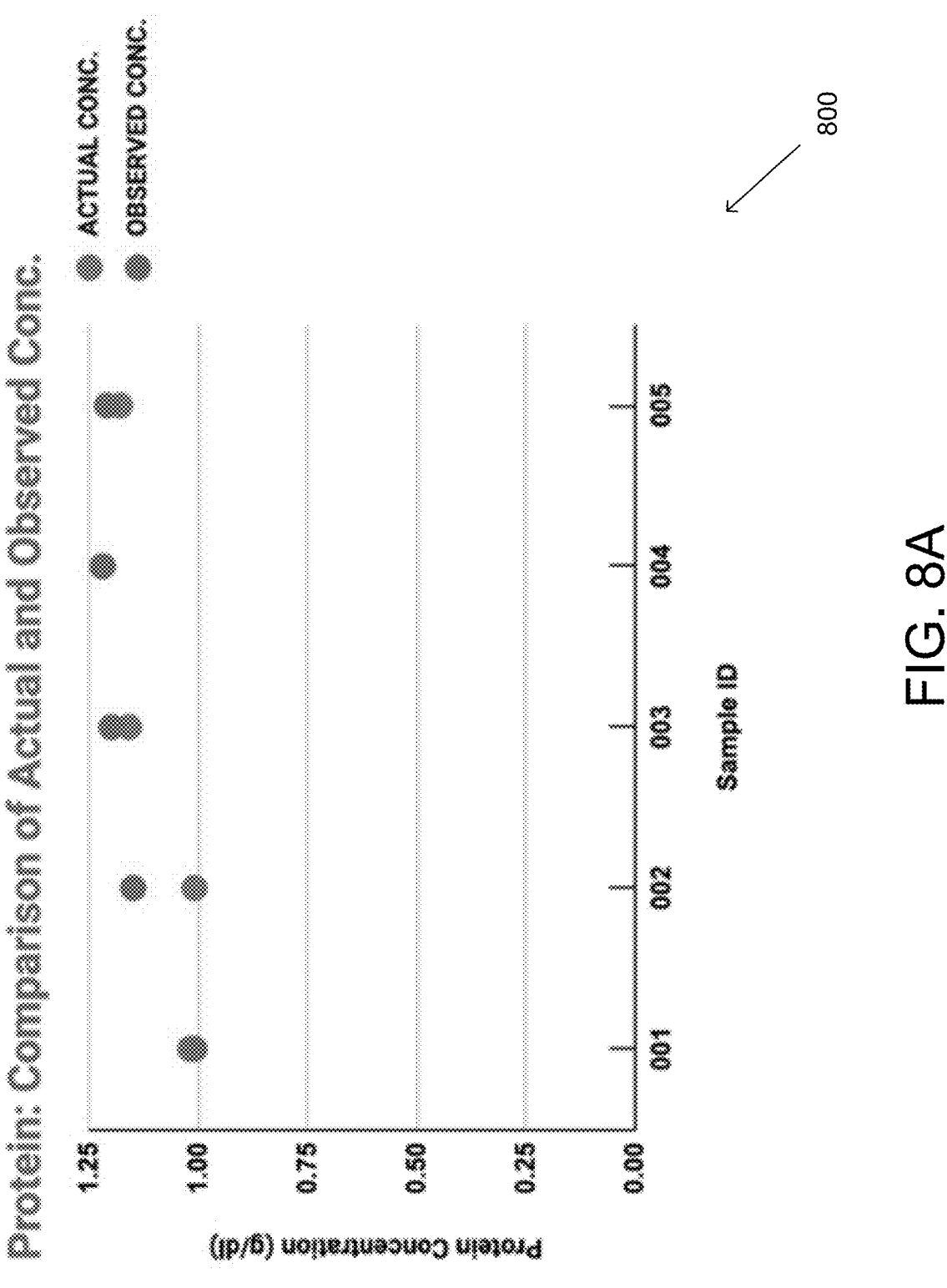
FIG. 8A illustrates a comparison of concentration of protein observed versus actual measured from a third-party lab in accordance with an embodiment of the invention.
Figure 8B:
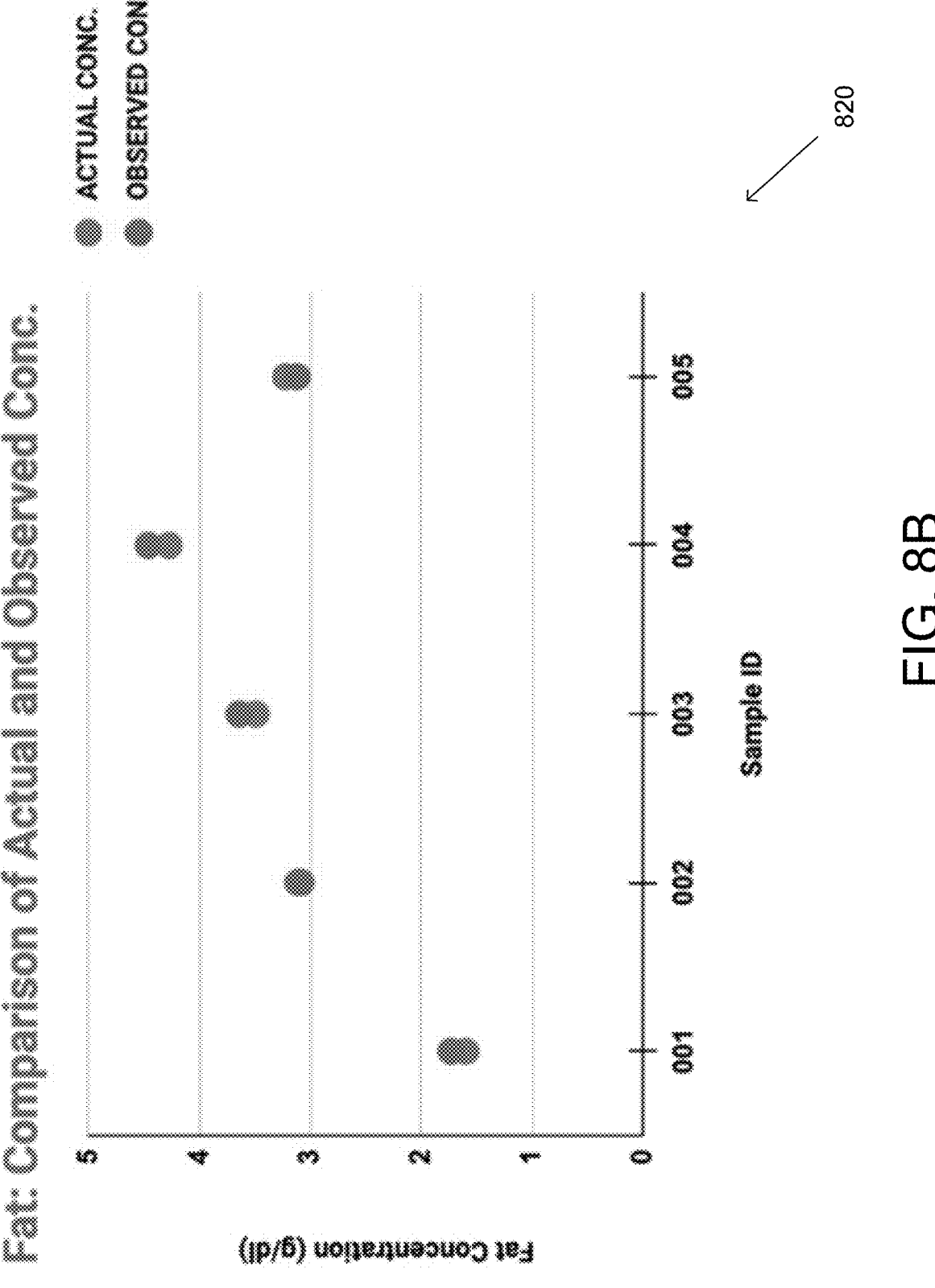
FIG. 8B illustrates a comparison of concentration of fat observed versus actual measured from a third-party lab in accordance with an embodiment of the invention.
Figure 8C:
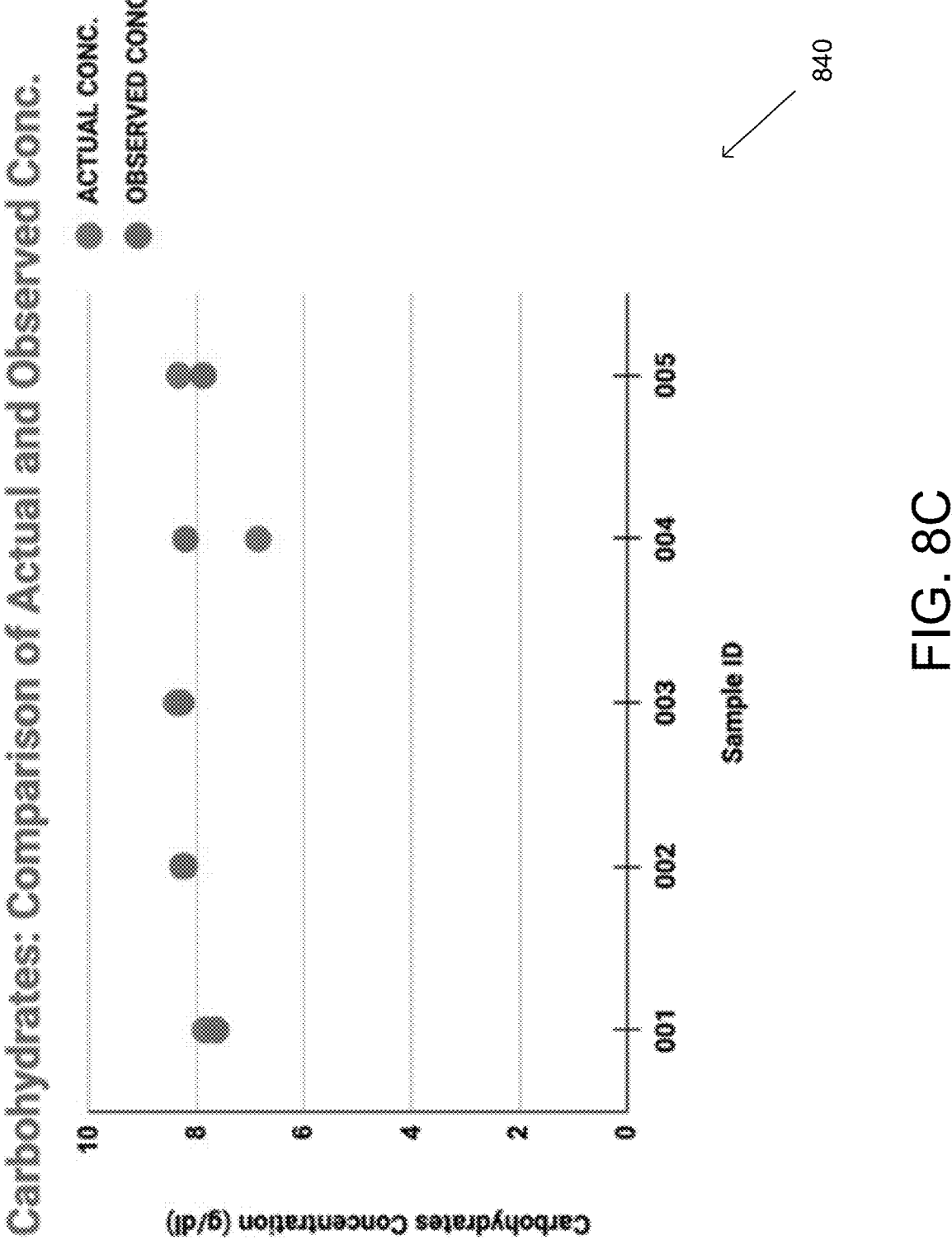
FIG. 8C illustrates a comparison of concentration of carbohydrates observed versus actual measured from a third-party lab in accordance with an embodiment of the invention.

An example comparison of concentration of protein, fat and carbohydrates observed versus actual measured from a third-party lab in accordance with an embodiment of the invention is shown in FIGS. 8A-8C, respectively. As an example, five samples are used for the comparison. In FIGS. 8A-8C, an x-axis represents a sample ID which is from 001-005, and a y-axis represents a concentration of respective protein, fat and carbohydrates in g/dl. In some embodiments, the mean value of the extracted color was used to determine the observed concentration to compare the performance of the present processes/software against the third-party lab. As shown in FIGS. 8A-8C, there is no statistical difference in the color extracted or the measured concentration for each test strip under varying lighting conditions, proving the efficacy of the color correction processes.

Based on the comparison between the observed concentration and the actual concentration, an error rate and a mean difference are calculated for the present breast milk analyses. Typically, the error rate for the observed concentration of protein is ±4.17%, and the mean difference is 0.04 g/dl. The error rate for the observed concentration of fat is ±4.19%, and the mean difference is 0.12 g/dl. The error rate for the observed concentration of carbohydrates is ±5.86%, and the mean difference is 0.43 g/dl. Those error rates and mean differences are tolerable.

Although a specific accuracy testing and validation method is discussed above with respect to FIGS. 8A-8C, any of a variety of accuracy testing and validation methods as appropriate to the requirements of a specific application can be utilized in accordance with embodiments of the invention. Processes for Testing Breast Milk in accordance with embodiments of the invention are discussed further below.

Processes for Testing Breast Milk

A flow chart illustrating a process for testing breast milk for macronutrient concentration(s) using a test strip in accordance with an embodiment of the invention is shown in FIG. 9. The process 900 may include capturing (902) image data of a test trip. In many embodiments, a camera may be used to capture (902) image data of the test strip. The process 900 may also include identifying (904) at least one region associated with a macronutrient. The process 900 may also include analyzing (906) the at least one region associated with a macronutrient. In some embodiments, the analyzing (906) may include measuring an absorbance of the test trip to quantify macronutrient profiles. In various embodiments, the absorbance may be a measure of how much light of a certain wavelength specific to the experiment passes through a solution versus how much is absorbed by the solution. In some embodiments, the analyzing (906) may include spectroscopic analysis of the scattered light spectrum from the test strips and/or a region of the test strips which can reveal subtle features that are not visually quantifiable and can be used to provide more precise information. The process 900 may also include displaying (908) at least one macronutrient concentration.

A flow chart illustrating a process for analyzing (906) a first region of a test strip for protein concentration in accordance with an embodiment of the invention is shown in FIG. 10. The process 1000 may include selecting (1002) a first region of the test strip. The process 1000 may also include calculating (1004) a spectrum value associated with a color in the first region. In some embodiments, digital color information may be obtained in RGB color space. In some embodiments, a color channel that gives a higher net signal is chosen for the region. The process 1000 may also include converting (1006) the spectrum value to a protein concentration, as further described above. In some embodiments, the concentration data may measure a mean intensity of color developed on the first region of the test strip. In some embodiments, the concentration values may be mean±standard deviation.

Figure 11:
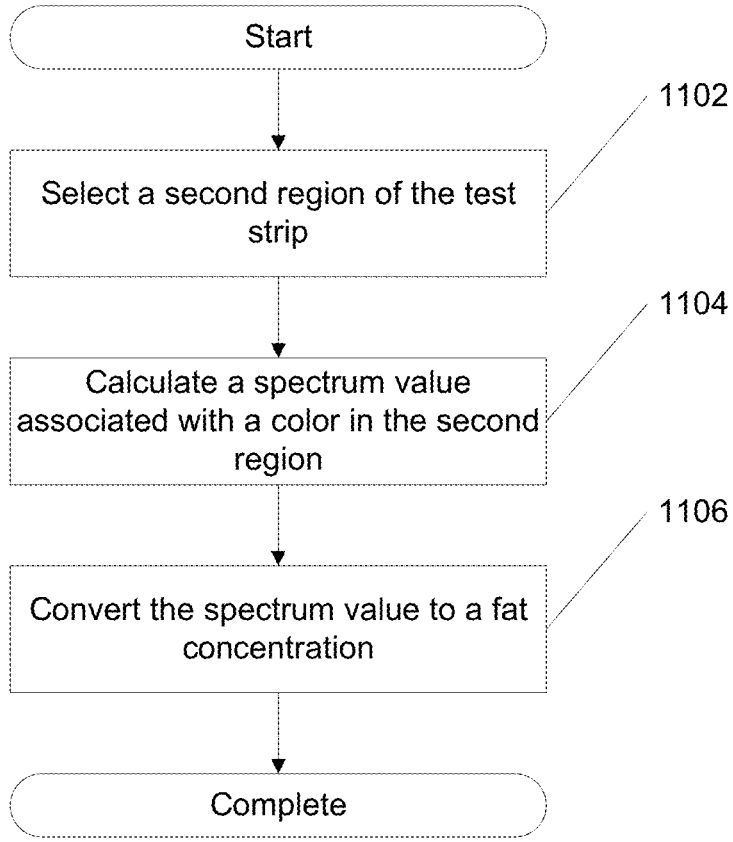
FIG. 11 is a flow chart illustrating a process for analyzing a second region of a test strip for fat concentration in accordance with an embodiment of the invention.

A flow chart illustrating a process for analyzing (906) a second region of a test strip for fat concentration in accordance with an embodiment of the invention is shown in FIG. 11. The process 1100 may include selecting (1102) a second region of the test strip. The process 1100 may also include calculating (1104) a spectrum value associated with a color in the second region. In some embodiments, digital color information may be obtained in RGB color space. In some embodiments, a color channel that gives a higher net signal is chosen for the region. The process 1100 may also include converting (1106) the spectrum value to a fat concentration, as further described above. In some embodiments, the concentration data may measure a mean intensity of color developed on the second region of the test strip. In some embodiments, the concentration values may be mean±standard deviation.

Figure 12:
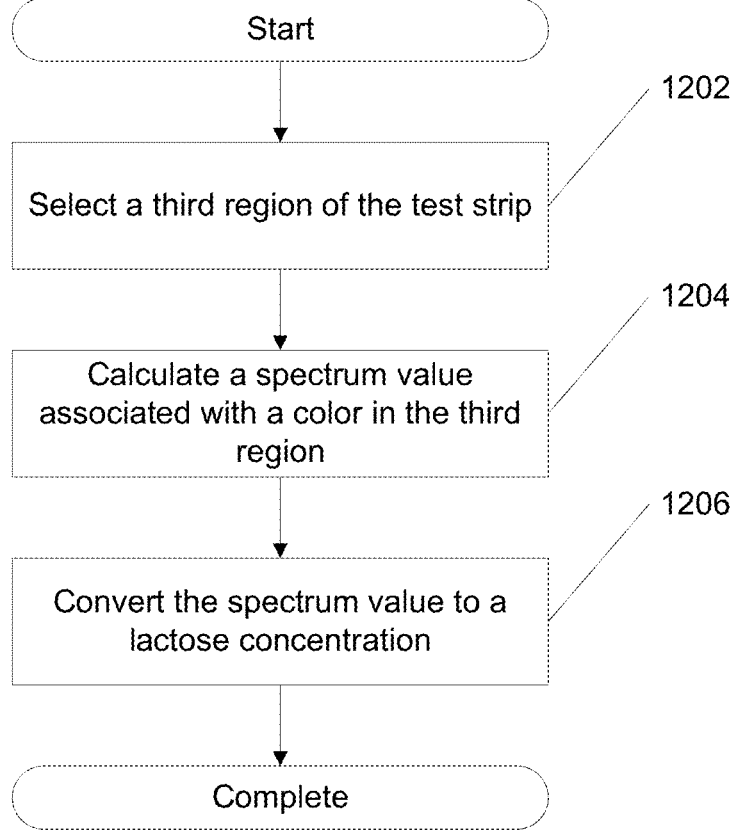
FIG. 12 is a flow chart illustrating a process for analyzing a third region of a test strip for lactose concentration in accordance with an embodiment of the invention.

A flow chart illustrating a process for analyzing a third region of a test strip for lactose concentration in accordance with an embodiment of the invention is shown in FIG. 12. The process 1200 may include selecting (1202) a third region of the test strip. The process 1200 may also include calculating (1204) a spectrum value associated with a color in the third region. In some embodiments, digital color information may be obtained in RGB color space. In some embodiments, a color channel that gives a higher net signal is chosen for the region. The process 1200 may also include converting (1206) the spectrum value to a lactose concentration, as further described above. In some embodiments, the concentration data may measure a mean intensity of color developed on the third region of the test strip. In some embodiments, the concentration values may be mean±standard deviation.

Although specific processes are discussed above with respect to FIGS. 9-12, any of a variety of steps as appropriate to the requirements of a specific application can be utilized in accordance with embodiments of the invention. While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A color-based strip, comprising:
a protein reagent pad comprising sodium bicinchoninate and cupric sulfate, wherein the protein reagent pad is configured to undergo a first reaction comprising a green-to-purple color change when the protein reagent pad contacts a sample, wherein the green-to-purple color change is proportional to a protein concentration of the sample, and is configured to generate a linear protein calibration curve from standardized protein concentrations of about 1.0 g/dl to about 1.6 g/dl;
a fat reagent pad comprising a pink dye indicator, lipoprotein lipase, glycerol phosphate oxidase, horseradish peroxidase, and galactose kinase, wherein the fat reagent pad is configured to undergo a second reaction comprising an off white-to-pink color change when the fat reagent pad contacts the sample, wherein the off white-to-pink color change is proportional to a fat concentration of the sample, and is configured to generate a linear fat calibration curve from standardized fat concentrations of about 1.5 g/dl to about 5.0 g/dl; and
a lactose reagent pad comprising beta-galactosidase, peroxidase and galactose oxidase, wherein the lactose reagent pad is configured to undergo a third reaction comprising a light green to blue then yellow color change when the lactose reagent pad contacts the sample, wherein the light green to blue then yellow color change is proportional to a lactose concentration of the sample, and is configured to generate a linear lactose calibration curve from standardized lactose concentrations of about 7.0 g/dl to about 9.0 g/dl.

2. The color-based strip of claim 1, wherein the sample comprises milk.

3. The color-based strip of claim 1, wherein the sample comprises breast milk.

4. A method for quantifying macronutrient content, comprising:
splitting an image of a protein reagent pad comprising sodium bicinchoninate and cupric sulfate that is located on a color-based strip into a first plurality of color channels, wherein the protein reagent pad has contacted a sample and has undergone a green-to-purple color change proportional to a protein concentration of the sample;
generating a first spectrum value from at least one first color channel from the first plurality of color channels; and
calculating a protein concentration value of the sample by comparing the first spectrum value to a linear protein calibration curve generated from protein concentration standards comprising concentrations of about 1.0 g/dl to about 1.6 g/dl protein;
splitting an image of a fat reagent pad comprising a pink dye indicator and one or more of lipoprotein lipase, glycerol phosphate oxidase, horseradish peroxidase, and galactose kinase that is located on the color-based strip into a second plurality of color channels, wherein the fat reagent pad has contacted the sample and has undergone an off white-to-pink color change proportional to a fat concentration of the sample;
generating a second spectrum value from at least one second color channel from the second plurality of color channels;
calculating a fat concentration value of the sample by comparing the second spectrum value to a linear fat calibration curve generated from fat concentration standards comprising concentrations of about 1.5 g/dl to about 5.0 g/dl fat;
splitting an image of a lactose reagent pad comprising one or more of beta-galactosidase, peroxidase and galactose oxidase that is located on the color-based strip into a third plurality of color channels, wherein the lactose reagent pad has contacted the sample and has undergone a light green to blue then yellow color change proportional to a lactose concentration of the sample;
generating a third spectrum value from at least one third color channel from the third plurality of color channels; and
calculating a lactose concentration value of the sample by comparing the third spectrum value to a linear lactose calibration curve generated from lactose concentration standards comprising concentrations of about 7.0 g/dl to about 9.0 g/dl lactose;
thereby calculating the macronutrient content of the sample.

5. The method of claim 4, wherein the at least one first color channel comprises a first red color channel, a first green color channel, or a first blue color channel.

6. The method of claim 4, wherein the at least one second color channel comprises a second red color channel.

7. The method of claim 4, wherein the sample comprises milk.

8. The method of claim 4, wherein the sample comprises breast milk.

* * * * *